(12) United States Patent
Mrva et al.

(10) Patent No.: US 7,996,092 B2
(45) Date of Patent: Aug. 9, 2011

(54) DEVICES, SYSTEMS, AND METHODS EMPLOYING A MOLDED NERVE CUFF ELECTRODE

(75) Inventors: Joseph J. Mrva, Euclid, OH (US); Kenneth P. Rundle, Independence, OH (US); Joseph W. Boggs, II, Carrboro, NC (US)

(73) Assignee: NDI Medical, Inc., Cleveland, OH (US)

( * ) Notice: Subject to any disclaimer, the term of this patent is extended or adjusted under 35 U.S.C. 154(b) by 1034 days.

(21) Appl. No.: 11/653,578

(22) Filed: Jan. 16, 2007

(65) Prior Publication Data

US 2008/0172116 A1   Jul. 17, 2008

(51) Int. Cl.
*A61N 1/18* (2006.01)

(52) U.S. Cl. ....................................................... 607/118

(58) Field of Classification Search .................... 607/118
See application file for complete search history.

(56) References Cited

U.S. PATENT DOCUMENTS

| | | | |
|---|---|---|---|
| 3,421,511 A | 1/1969 | Schwartz et al. | |
| 3,654,933 A | 4/1972 | Hagfors | |
| 3,774,618 A | 11/1973 | Avery | |
| 4,573,481 A | 3/1986 | Bullara | |
| 4,590,946 A | 5/1986 | Loeb | |
| 4,602,624 A | 7/1986 | Naples et al. | |
| 4,628,942 A | 12/1986 | Sweeney et al. | |
| 4,649,936 A * | 3/1987 | Ungar et al. ............. | 607/118 |
| 4,750,499 A | 6/1988 | Hoffer | |
| 4,920,979 A | 5/1990 | Bullara | |
| 4,926,875 A | 5/1990 | Rabinovitz et al. | |
| 4,934,368 A | 6/1990 | Lynch | |
| 4,940,065 A | 7/1990 | Tanagho et al. | |
| 5,095,905 A | 3/1992 | Klepinski | |
| 5,265,608 A | 11/1993 | Lee et al. | |
| 5,289,821 A | 3/1994 | Swartz | |
| 5,324,322 A | 6/1994 | Grill, Jr. et al. | |
| 5,344,438 A * | 9/1994 | Testerman et al. ............ | 607/118 |
| 5,400,784 A | 3/1995 | Durand et al. | |
| 5,487,756 A | 1/1996 | Kallesoe et al. | |
| 5,505,201 A | 4/1996 | Grill, Jr. et al. | |
| 5,531,778 A | 7/1996 | Maschino et al. | |
| 5,634,462 A | 6/1997 | Tyler et al. | |
| 5,741,319 A | 4/1998 | Woloszko et al. | |
| 5,824,027 A | 10/1998 | Hoffer et al. | |
| 5,895,360 A * | 4/1999 | Christopherson et al. .... | 600/529 |
| 5,899,933 A | 5/1999 | Bhadra et al. | |

(Continued)

OTHER PUBLICATIONS

Nerve Cuff Electrode With Shape Memory Alloy Armature: Design and Fabrication, Crampon et al., *Bio-Medical Materials and Engineering* 12 (2002) 397-410.

(Continued)

*Primary Examiner* — Scott M Getzow
*Assistant Examiner* — Amanda Patton
(74) *Attorney, Agent, or Firm* — Ryan Kromholz & Manion, S.C.

(57) ABSTRACT

Devices, systems, and methods for recording, and/or stimulation, and/or blocking of a nerve make use of a molded nerve cuff electrode. One or more electrodes are positioned in one or more frames within a casing. The exterior surface of the casing is wrapped in an insulating material, and the wrapped casing is positioned within a cover tube. One or more additional electrodes may be positioned anywhere outside of the casing. An applicator tool having a body to hold the molded nerve cuff in an expanded configuration is used to implant the cuff about a nerve.

11 Claims, 18 Drawing Sheets

U.S. PATENT DOCUMENTS

| | | | |
|---|---|---|---|
| 5,919,220 | A | 7/1999 | Stieglitz et al. |
| 5,938,596 | A * | 8/1999 | Woloszko et al. ............ 600/377 |
| 5,964,702 | A | 10/1999 | Grill et al. |
| 5,989,233 | A | 11/1999 | Yoon |
| 6,292,703 | B1 | 9/2001 | Meier et al. |
| 6,308,105 | B1 | 10/2001 | Duysens et al. |
| 6,456,866 | B1 | 9/2002 | Tyler et al. |
| 6,600,956 | B2 | 7/2003 | Maschino et al. |
| 6,907,295 | B2 | 6/2005 | Gross et al. |
| 2002/0193790 | A1 | 12/2002 | Fleischman et al. |
| 2004/0138609 | A1 | 7/2004 | Fukuta et al. |
| 2005/0277999 | A1 | 12/2005 | Strother et al. |
| 2006/0030919 | A1 | 2/2006 | Mrva et al. |
| 2007/0060955 | A1 * | 3/2007 | Strother et al. .................. 607/2 |

OTHER PUBLICATIONS

"New Easy to Install Nerve Cuff Electrode Using Shape Memory Alloy Armature", Crampon et al. *Artificial Organs*, 23(5):392-395, 1999.

"Neural Morphological Effects of Long-Term Implantation of the Self-Sizing Spiral Cuff Nerve Electrode", Romero et al., *Medical & Biological Engineering & Computing*, 2001, vol. 39, pp. 90-100.

"Cuff Electrodes for Chronic Stimulation and Recording of Peripheral Nerve Activity", Loeb et al., *Journal of Neuroscience Methods*, 64 (1996), 95-103.

"Chronic Response of the Rat Sciatic Nerve to the Flat Interface Nerve Electrode", Tyler et al., *Annals of Biomedical Engineering*, vol. 31, pp. 633-642. 2003.

"A Spiral Nerve Cuff Electrode for Peripheral Nerve Stimulation", Naples et al. *IEEE Transactions on Biomedical Engineering*, vol. 35, No. II, Nov. 1988.

"Spiral Nerve Cuff Electrode for Recordings of Respiratory Output", Sahin et al. *The spiral Nerve Cuff Electrode*, 1997 American Physiological Societ, pp. 317-322.

"A Nerve Cuff Technique for Selective Excitation of Peripheral Nerve Trunk Regions", Sweeney et al., *IEEE Transactions on Biomedical Engineering*, vol. 37 No. 7, Jul. 1990.

* cited by examiner

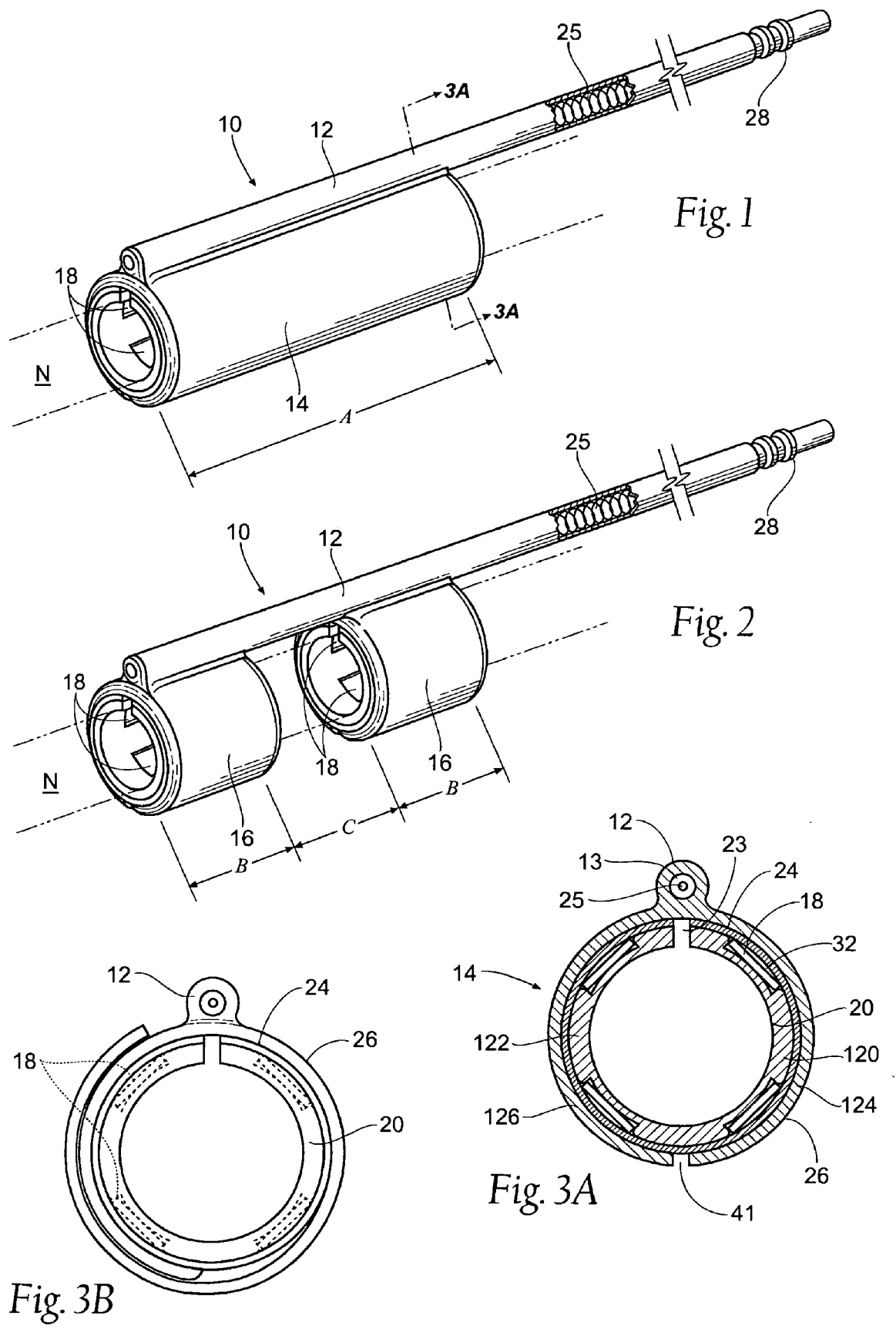

DEVICES, SYSTEMS, AND METHODS EMPLOYING A MOLDED NERVE CUFF ELECTRODE

STATEMENT REGARDING FEDERALLY SPONSORED RESEARCH

This invention may have been made with government support under grant no. 1RNS051862-01 awarded by the National Institutes of Health, through the National Institute of Neurological Disorders and Stroke. The Government may have certain rights in the invention.

FIELD OF THE INVENTION

The invention relates to nerve cuff electrodes for neuronal recording, stimulation, and blocking in animals, including humans.

BACKGROUND OF THE INVENTION

In the last forty years, neuromodulation and neurostimulation implantable technologies have been used extensively for a variety of indications. As such, the components of these systems have developed a significant track record and their actions on the body are reasonably well understood. Many of these systems use implantable pulse generators (IPGs) and electrodes to deliver charge to the site of a biological tissue, e.g., a muscle or a nerve. By using low frequency and/or high frequency waveforms, the system induces action potentials in a targeted nerve (or nerves) that create the desired effect. It should be noted that the ability to create action potentials does not necessarily require direct contact with the nerve; however, certain applications may be most effective with direct nerve contact. One example is selective stimulation or recording from a portion of a nerve bundle. Another example is the blocking of conduction of action potentials using high frequency signals.

One example of a cuff electrode is a spiral cuff electrode that was patented in 1986 by Naples, Mortimer, et al (U.S. Pat. No. 4,602,624). It is a laminated assembly of two Silastic sheets (Dow Corning), with one layer stretched during the glue-up process (Silastic Adhesive). Once the assembly is freed from the press, it naturally curls towards the stretched side. The flat edge is typically long enough so that the cuff makes at least one and half revolutions of the nerve. This seals the cuff to provide an insulation barrier so that current does not leak around the cuff. The two laminates carry platinum electrodes, with spacing cut out on the stretched side so that current can be conducted inwards.

Some existing cuff electrodes do not reliability interface to small nerves. The stiffness of the platinum prevents the electrode from fully conforming to the small diameter of the nerve. The stiffness also does not allow the electrode to be fully adaptive, accommodating post-operative swelling of the nerve, which commonly occurs. Furthermore, the manufacturing process described in the Naples et al. patent to produce the electrode is hand-labor intensive with low repeatability of key process parameters.

Another example of a cuff electrode is a split cylinder cuff electrode that was patented in 2003 by Maschino et al. (U.S. Pat. No. 6,600,956). The split cuff configuration includes an electrode supporting matrix that supports a plurality of circumferential metallic electrodes. The matrix is injection molded to normally assume a curled, cuff shape. A split in the cuff allows the cuff to be opened to encircle a portion of a nerve. Once positioned, a fastener system is incorporated to close the cuff to prevent separation from the nerve. The fastener system reduces the ability of the cuff to expand about the nerve due to swelling, for example.

It is time that devices, systems, and methods employing a molded nerve cuff electrode provide improved manufacturability, consistent closing about the target nerve, and include the means to controllably manage increase or decrease in nerve size while maintaining the electrode to nerve contact pressure.

SUMMARY OF THE INVENTION

The invention provides improved assemblies, systems, and methods for neuronal recording, stimulation, and blocking in animals, including humans.

One aspect of the invention provides an implantable cuff electrode for placement about a biological tissue, such as a nerve. The implantable cuff electrode comprises an inner elastic body, the inner elastic body having at least one aperture sized and configured to accept at least one electrically conductive surface. The at least one electrically conductive surface is positioned in the at least one aperture and configured to allow contact between the electrically conductive surface and the biological tissue to be surrounded. The implantable cuff electrode further comprises an insulating material positioned over the inner elastic body and the at least one electrically conductive surface, and a cover tube positioned over the insulating material. The insulating material is secured to at least a portion of the inner elastic body, and the cover tube is secured to at least a portion of the insulating material.

An additional aspect of the invention provides an implantable cuff electrode where the inner elastic body includes a longitudinal split extending the length of the inner elastic body, and where the cover tube includes a longitudinal split extending the length of the cover tube. The inner elastic body may comprise an expansion portion and a non-expansion portion. The cover tube may also comprise an expansion portion and a non-expansion portion. The cover tube may extend in a range of about 350 degrees to about 540 degrees from end to end.

In one aspect of the invention, the implantable cuff electrode further includes at least one additional electrically conductive surface that is positioned away from an inside surface of the cuff, the at least one additional electrically conductive surface being in electrical conductive contact with the at least one electrically conductive surface positioned in the inner elastic body.

In an additional aspect of the invention, the assemblies, systems, and methods provide an inner elastic body including a longitudinal split extending the length of the inner elastic body and a cover tube including a longitudinal split extending the length of the cover tube. The inner elastic body longitudinal split and the cover tube longitudinal split may be out of phase and are sized and configured to provide an access point to open the cuff electrode for placement about the biological tissue.

In yet an additional aspect of the invention, the assemblies, systems, and methods provide a cover tube including at least one aperture sized and configured to accept at least one cover tube electrically conductive surface. The at least one cover tube electrically conductive surface may be positioned in the at least one aperture in the cover tube and configured so there is no intimate contact between the cover tube electrically conductive surface and the biological tissue surrounded.

In another aspect of the invention, the assemblies, systems, and methods provide a method of manufacturing a cuff electrode comprising conductively coupling at least one wire to at least one electrically conductive surface, positioning the at least one electrically conductive surface in an aperture within an inner elastic body, placing an insulating material around at least a portion of the inner elastic body, and positioning a cover tube over the assembled inner elastic body, at least one electrically conductive surface, and insulating material. Positioning the cover tube may include securing the cover tube to at least a portion of the insulating material using an implantable bonding technique. Positioning the at least one electrically conductive surface may include securing the electrically conductive surface in the aperture of the inner elastic body using an implantable bonding technique. Placing an insulating material may further include securing the insulating material to at least a portion of the inner elastic body using an implantable bonding technique.

In yet another aspect of the invention, the assemblies, systems, and methods provide a system for neuronal recording and/or stimulating and/or blocking. The system comprises an implantable lead having a proximal end and a distal end, and a cuff electrode coupled to the distal end of the lead. The cuff electrode comprises an inner elastic body, the inner elastic body having at least one aperture sized and configured to accept at least one electrically conductive surface, the at least one electrically conductive surface positioned in the at least one aperture and configured to allow contact between the electrically conductive surface and a biological tissue to be surrounded, an insulating material positioned over the inner elastic body and the at least one electrically conductive surface, and a cover tube positioned over the insulating material. The lead encapsulates a wire element extending from the at least one electrically conductive surface to the proximal end of the lead, and the proximal end of the lead is coupled to a stimulation pulse generator. The proximal end of the lead may comprise an implantable IS-1 connector. The system may also include means to anchor the distal portion of the lead to surrounding tissue.

BRIEF DESCRIPTION OF THE DRAWINGS

FIG. 1 is a perspective view of one embodiment of an implant system including a lead and a molded split nerve cuff electrode implanted about a nerve.

FIG. 2 is a perspective view of an additional embodiment of an implant system, the system including a lead and a molded split nerve cuff electrode implanted about a nerve, the nerve cuff including more than one nerve cuff segment.

FIG. 3A is a section view of the molded nerve cuff taken generally along line 3A-3A in FIG. 1.

FIG. 3B is an end view of an alternative embodiment of the molded nerve cuff of FIG. 1, showing the cuff extending about 1.5 revolutions around the nerve.

Figure 4A:
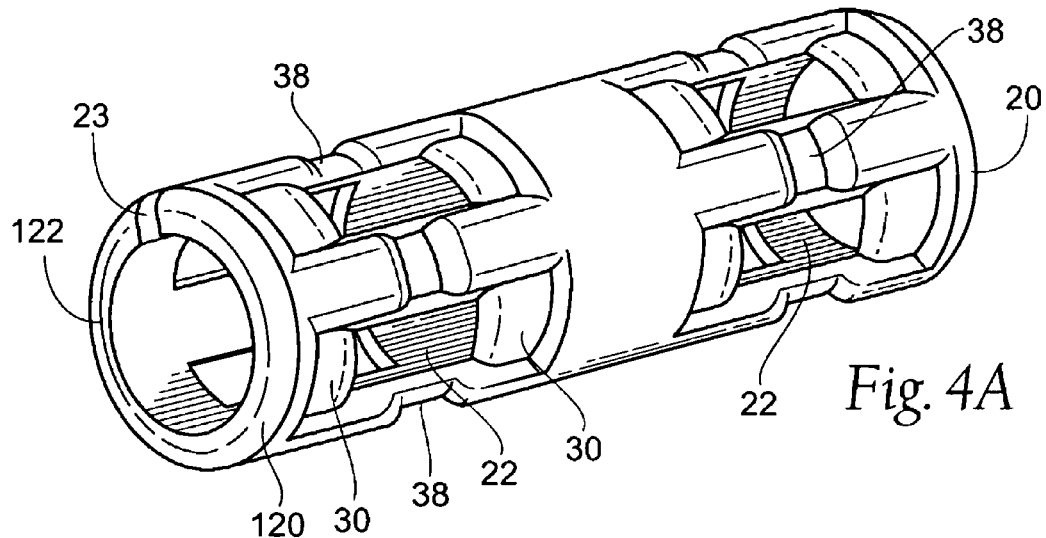
FIG. 4A is a perspective view of a split casing component having one or more frames and used to hold one or more electrodes in position, the casing used with the nerve cuff shown in FIG. 1.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the desired embodiment has been described, the details may be changed without departing from the invention, which is defined by the claims.

I. Molded Nerve Cuff

FIGS. 1 and 2 show an implant system 10 for recording, and/or stimulation, and/or blocking of a biological tissue, i.e., a nerve N in an animal, including a human. The system 10 includes an implantable lead 12 having a proximal and a distal end. The distal end of the lead 12 carries a split cuff 14 (see FIG. 1), or more than one split cuff 16 (two cuff segments are shown in FIG. 2). Within the cuff 14, 16, are positioned one or more electrodes 18. Split cuff 14 may include longitudinal lengths "A" ranging about 6 mm to about 10 mm, and in one application, "A" is about 8 mm. Split cuff 16 may include longitudinal lengths "B" ranging about 3 mm to about 5 mm, with a gap "C" ranging about 2 mm to about 4 mm, and in one application, "B" is about 4 mm and "C" is about 3 mm.

The configuration of the cuff 14 and the cuff 16 may be the same or similar, and both 14 and 16 may comprise a multi-layered molded cuff. AS such, the following description will reference cuff 14, although it is to be appreciated that this description embodies cuff 16 as well. As FIG. 3A shows, the cuff 14 includes a flexible molded split casing 20, which may have an elastic memory. The split casing 20 comprises an expansion portion 120 and a non-expansion portion 122. The expansion portion 120 allows the cuff 14 to be expanded or opened to position the cuff over a nerve, as will be described in greater detail later.

The exterior surface of the casing 20 and electrode(s) 18 seated within the casing 20 are covered with a thin layer of insulating material 24, e.g., about 0.001 inch to about 0.005 inch thick silicone, Teflon, or polyurethane, to provide electrical insulation for the non-tissue facing side 32 of the electrode 18. The casing 20, electrodes 18, and insulation 24, are positioned within a molded split cover tube 26, which may also have an elastic memory. Assembly of the cuff 14 will be described in greater detail in Section II below. As with the split casing 20, the split cover tube 26 also comprises an expansion portion 124 and a non-expansion portion 126. The expansion portion 124 allows the cuff 14 to be expanded or opened to position the cuff over a nerve, as will be described in greater detail in Section III below. The molded cover tube 26 is coupled to or includes the distal portion of the lead 12. The insulating material 24 also provides lubricity between the casing 20 and the cover tube 26 to allow the two surfaces to slide or adjust, i.e., open or close, during implantation and changes in nerve size. A lumen 13 within the lead 12 is provided to allow a lead wire or wires 25 to extend from the electrode 18 to a connector 28 on the proximal end of the lead 12. The lumen 13 may also accommodate the insertion of a guide wire to facilitate lead placement.

Figure 4B:
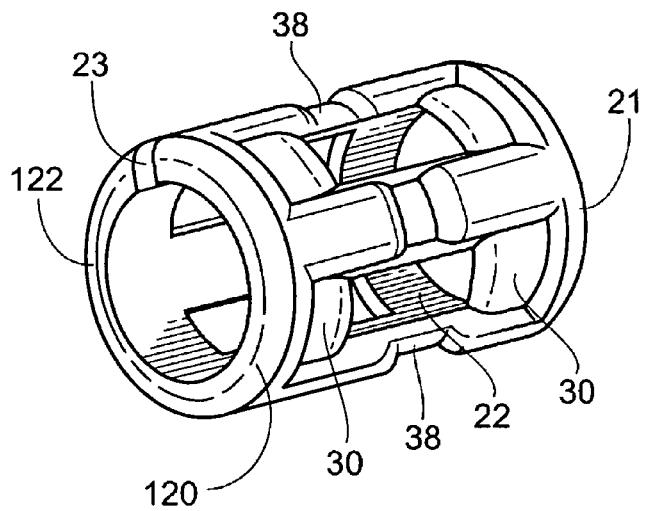
FIG. 4B is a perspective view of an alternative embodiment of a split casing component having one or more frames and used to hold one or more electrodes in position, the casing used with the nerve cuff shown in FIG. 2.

As seen in FIGS. 4A and 4B, the casings 20 and 21 may be molded from a low durometer elastomer material, e.g., silicone or polyurethane, and includes one or more apertures or frames 22 to position and support a corresponding electrode 18. As can be seen, the casing 20 includes eight frames 22, although more or less may be used. A longitudinal split 23 extending the length of the casing 20 provides an expandable access point to position the cuff 14 over the target nerve N. Positioning the cuff 14, 16 over a target nerve N will be described in greater detail later. FIG. 4B shows the casing 21 used with cuff 16, and shows four frames 22, although more or less may be used. As can be seen, the casing 21 includes the longitudinal split 23, and a single row of one or more longitudinally spaced frames 22 positioned around the circumference of the casing 21.

Figure 5:
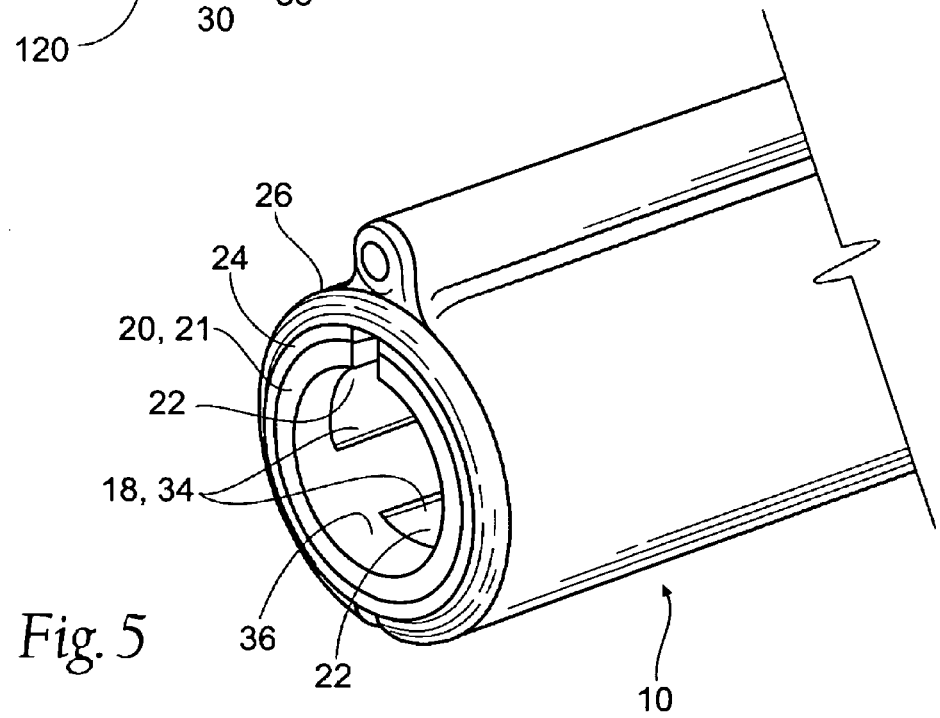
FIG. 5 is a perspective view of the distal end of the nerve cuff shown in FIG. 1, showing the positioning of the nerve facing side of an electrode.
Figure 6A:
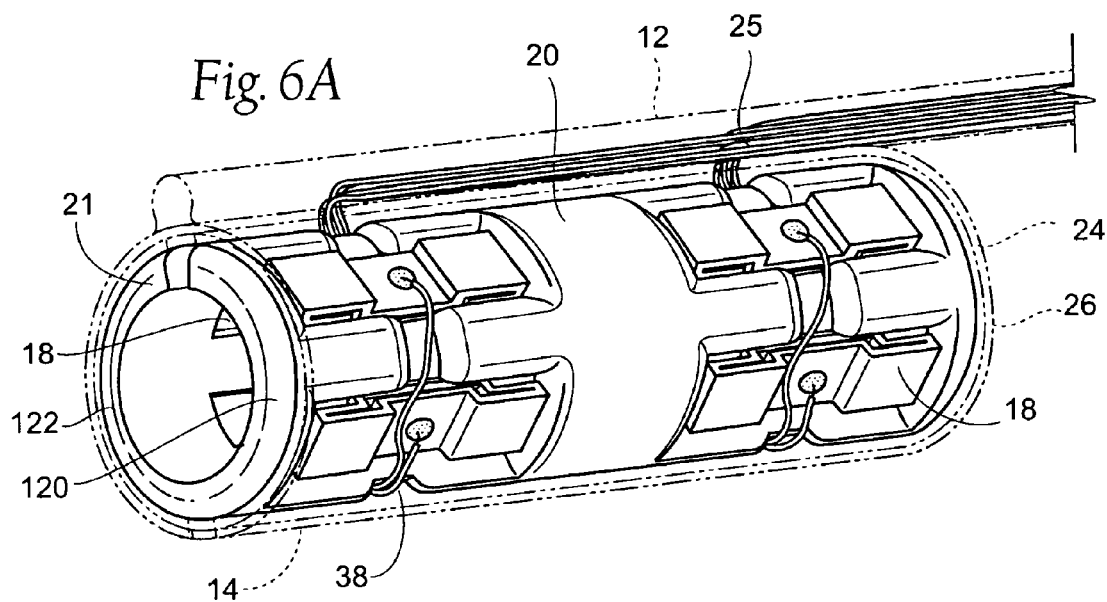
FIG. 6A is a perspective view of the split casing component shown in FIG. 4A, having electrodes positioned in the frames and lead wires extending from each electrode, through a channel, and into a lumen within the lead.
Figure 6B:
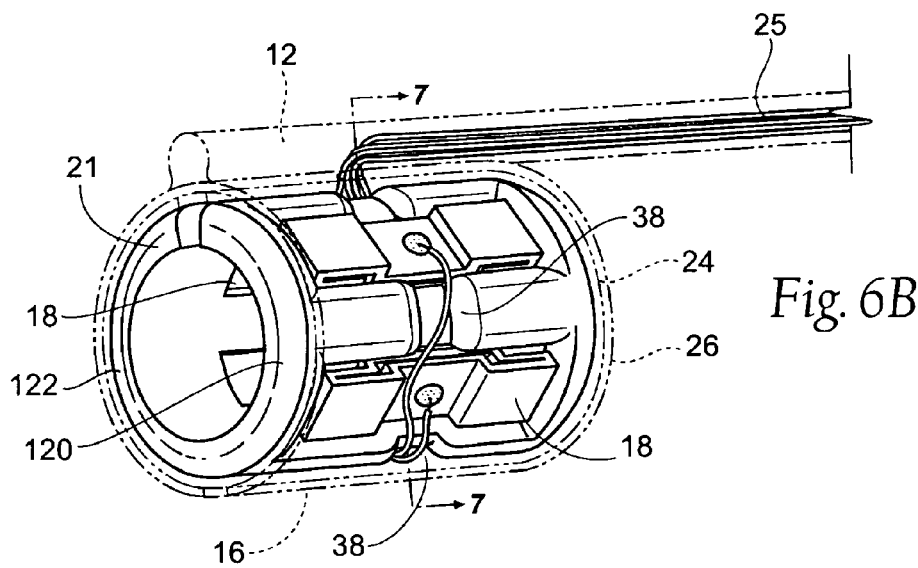
FIG. 6B is a perspective view of the split casing component shown in FIG. 4B, having electrodes positioned in the frames and the lead wires extending from each electrode, through a channel, and into a lumen within the lead.
Figure 7:
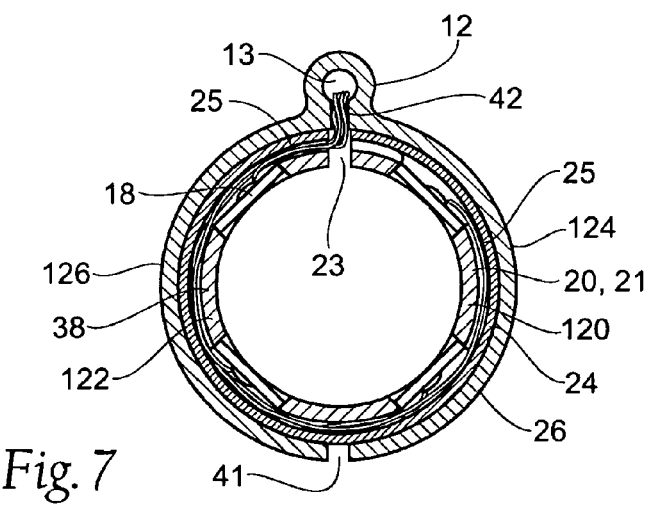
FIG. 7 is an end section view of the molded nerve cuff taken generally along line 7-7 in FIG. 6B.

Casing 20 includes two (or more) rows of one or more longitudinally spaced frames 22 positioned around the circumference of the casing 20. Each frame 22 includes support structure 30 to allow the electrode 18 to be positioned within the frame 22 and extend through the casing 20, 21 a predetermined amount (see FIG. 5). The tissue facing side 34 of the electrode 18 may extend beyond the inner surface 36 of the casing 20, 21 or may be flush with the inner surface. 36, or may be recessed within the frame 22, as shown. Each frame also includes at least one channel 38 extending to an adjacent frame and to the longitudinal split 23. The channel 38 is sized and configured to provide a path for the lead wire 25 to extend from the electrode 18 in a frame 22, around the casing 20, and into the lead 12 (see FIGS. 6A to 7).

The lead wire(s) 25 may be a straight wire, such as implant grade stainless steel or MP35N, as non-limiting examples, or the lead wire 25 may be coiled to a small diameter. The coiled lead wire may allow for additional flexibility of the cuff 14, because the coiled wire would allow for easier stretching than the straight wire, which in turn may cause less pressure on the nerve as the nerve diameter changes. The lead wires 25 may be coupled to the electrodes using a variety of common techniques, such as crimping, laser welding, and resistance welding, for example.

Figure 8:
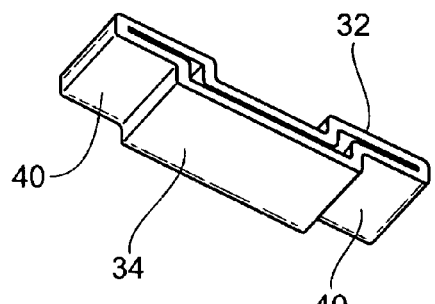
FIG. 8 is a perspective view of an electrode used with the molded nerve cuff shown in FIG. 1, the electrode including a pair of flanges for support within the nerve cuff.

The electrodes 18 may be manufactured using Platinum or a Platinum Iridium mix (e.g., 90/10 or 80/20), for example, and may be a solid component or a layered component formed using conventional metal forming techniques. In addition, these or alternative configurations may be manufactured using a thin film of metal deposited on a liquid crystal polymer substrate. As can be seen in FIG. 8, the electrode includes a non-nerve facing side 32 and a nerve facing side 34. The electrode 18 is sized and configured to fit snugly within a corresponding frame 22 and includes a pair of flanges 40 to support the electrode within the frame. The electrode 18 may also be glued or otherwise secured in place. The flanges 40 (and the corresponding support structure 30) allow the electrode 18 to sit snugly within the frame 22.

The electrodes 18 may measure about 4 mm of length along the axis of the nerve N and about 2 mm of width along the circumference of the nerve N. In one representative embodiment, the electrodes 18 each measure about 1.5 mm×0.75 mm in length and width, respectively. In the illustrated embodiment, the electrically conductive surfaces 18 are carried in an exposed array positioned longitudinally along the axis of the nerve N. This geometry is well suited for applying nerve conduction blocks, but has application for use in other indications as well. Other geometries, sizes, and configurations can, of course, be used for other indications.

Figure 9:
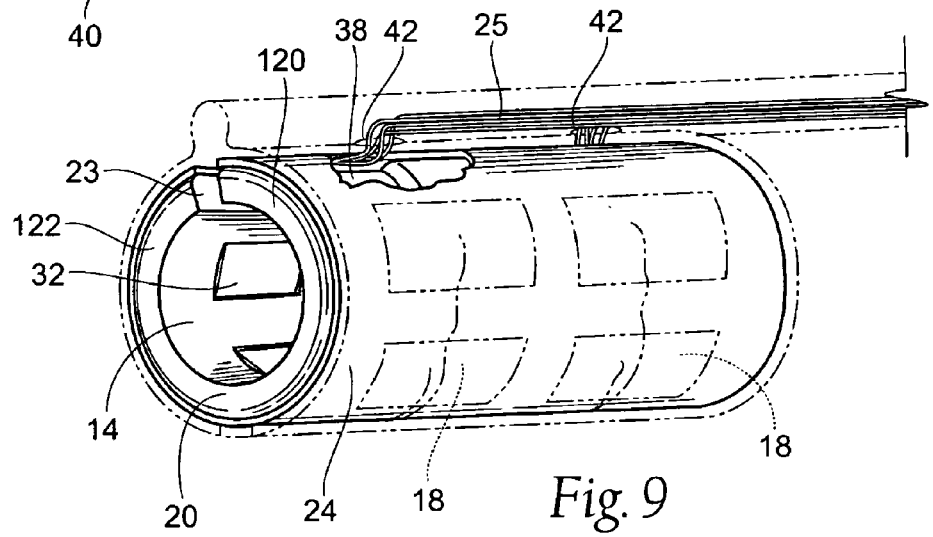
FIG. 9 is a perspective view of the split casing component shown in FIG. 6A, and having electrodes positioned in the frames with the casing and electrodes covered with an insulating material, and the split cover tube shown in phantom.

With the electrodes 18 positioned within their respective frames 22., and the lead wires 25 positioned within a channel 38 and wrapped around the casing 20, a thin layer of insulating material 24 is positioned over the casing 20 (see FIG. 9) The insulating material 24 may be secured using known implantable bonding techniques (e.g., glued, sonic, heat, or bonded) to the casing 20. The lead wires 25 wrap around the casing starting on the casing expansion portion 120 and extend along the casing non-expansion portion 122 and under the insulating material until the lead wires 25 exit at the longitudinal split 23.

Figure 10A:
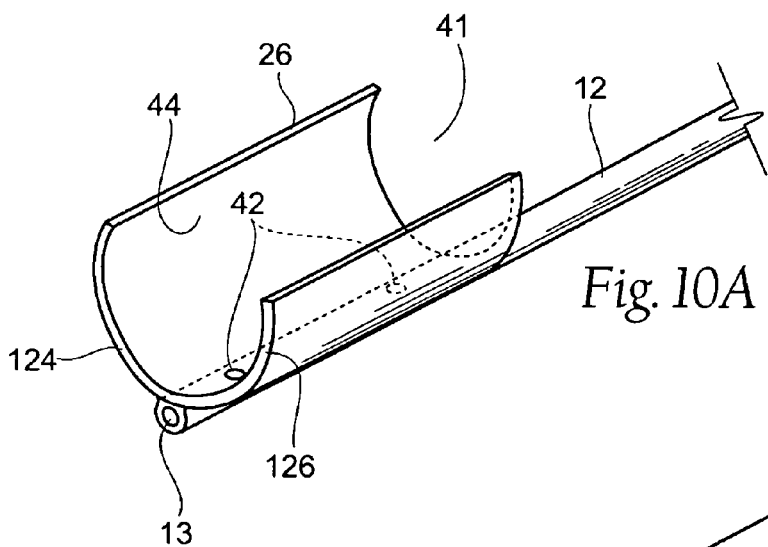
FIG. 10A is an interior perspective view of a split cover tube component used with the nerve cuff shown in FIG. 1, the cover tube coupled to the distal end of the lead and used to hold the casing and insulating material in position.
Figure 10B:
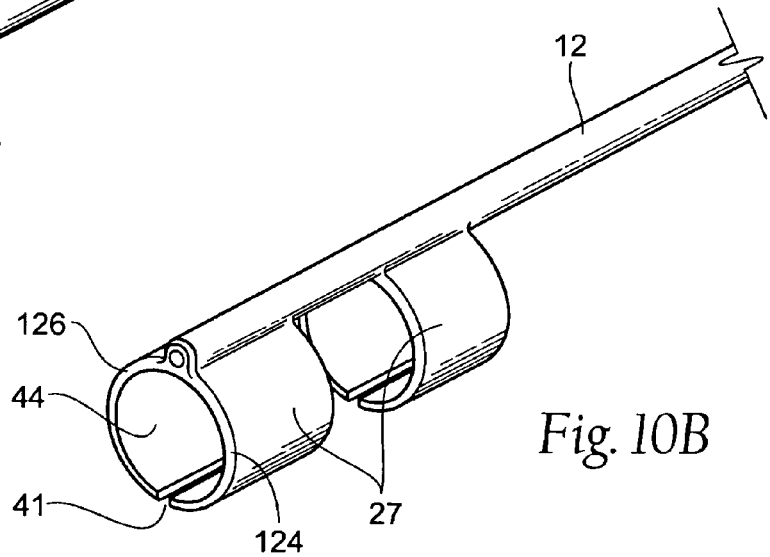
FIG. 10B is a perspective view of an alternative embodiment of a split cover tube component, the cover tube used with the nerve cuff shown in FIG. 2, the cover tube coupled to the distal end of the lead and used to hold the casing and insulating material in position.

As previously described for cuff 14, the casing 20, electrodes 18, and insulation 24, are positioned within the molded cover tube 26 with the longitudinal split 23 positioned generally adjacent to the lead 12 (see FIG. 3A). The molded cover tube 26 may be molded from a low durometer elastomer material, e.g., silicone or polyurethane. As seen in FIG. 10A, the molded cover tube 26 is coupled to or is integral with the distal portion of the lead 12, and includes a longitudinal split 41 extending the length of the cover tube. FIG. 10A shows the split 41 of the molded cover tube 26 spread open. FIG. 10B shows the molded cover tube 27 for cuff 16, and having the longitudinal split 41 extending the length of each cuff 16. At least one aperture 42 is positioned at the inner surface 44 of the cover tube 26, 27, to allow the lead wire 25 to extend from the electrode 18 through a channel 38 and into the lumen 13 (see FIG. 7 and 10A). The lead wire 25 then extends to the connector 28 on the proximal end of the lead 12.

The molded components of the cuff 14, 16, i.e., the casing 20, the insulation 24, and the cover tube 26, is shaped or formed during the molding process to normally assume the generally split cylinder configuration. The split cylinder cuff circumference may comprise about 360 degrees, as shown in FIG. 3A, or may be more than 360 degrees, such as about 540 degrees, as shown in FIG. 3B.

Each cuff 14, 16 can be elastically opened along the casing split 23 and the cover tube split 41 to increase its inner diameter (as will be described later), e.g., to be initially fitted about the periphery of the nerve N, and in response to post-operative changes in the diameter of the nerve N that might occur due to swelling. The elasticity of the cuff positions the electrodes 18 gently against the periphery of the targeted nerve N. The elasticity of the cuff is selected to gently wrap about the nerve N without causing damage or trauma. To this end, it is believed desirable that the elastic memory of the cuff exhibits a predictable and repeatable pressure vs. diameter relationship that gradually increases pressure with increase in diameter to allow the cuff electrode to fit gently about the periphery of a nerve, and not too tightly to cause damage (i.e., exerts a maximum pressure about the nerve N that does not exceed about 20 mmHg).

The implantable lead 12 (see FIGS. 11 to 13) comprises a molded or extruded component 46, which may encapsulate or enclose (in the case of a tubular construction) the straight or coiled (as shown) wire element 25, and the plug or connector 28 (shown in FIG. 1). The lead 12 may be composed of one wire 25 connecting a single electrode 18 to contact(s) of the connector 28. Alternatively, the lead 12 may be composed of several individually insulated wires 25 connecting multiple electrodes 18 to multiple contacts of the connector 28. Each wire may be a single strand of metal, such as MP35N nickel-cobalt, or 316L stainless steel, or a more complex structure such as a drawn tube of MP35N or 316L filled with silver. Alternatively, each separate insulated wire may be composed of multiple strands of wire (four such strands are shown in FIG. 13), with each strand electrically connected in parallel at the electrode end and at the connector end. Examples of suitable electrical insulation include polyimide, parylene, and polyurethane. The molded or extruded lead 12 can have an outside diameter as small as about one (1) mm. The lead 12 may also include lumen 13 to allow for insertion of a guide wire to facilitate lead placement. The lead 12 may be approximately 10 cm to 40 cm in length, although lengths extending an anatomical furthest distance, i.e., the length of the body, are possible. The lead 12 provides electrical continuity between the connector 28 and the electrode 18.

Figure 11:
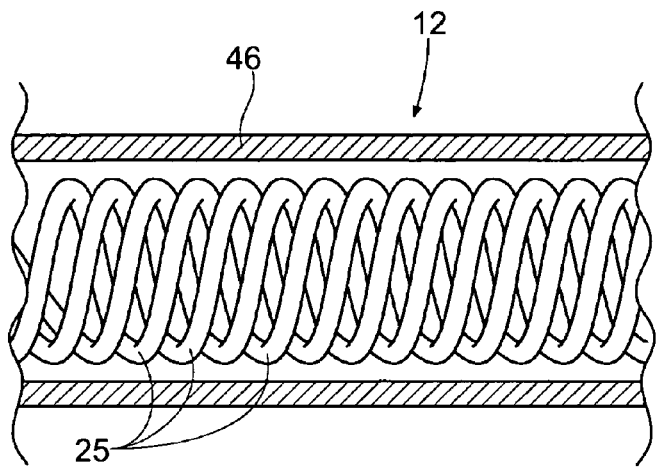
FIGS. 11 and 12 are side interior views of representative embodiments of a lead of the type shown in FIG. 1.
Figure 12:
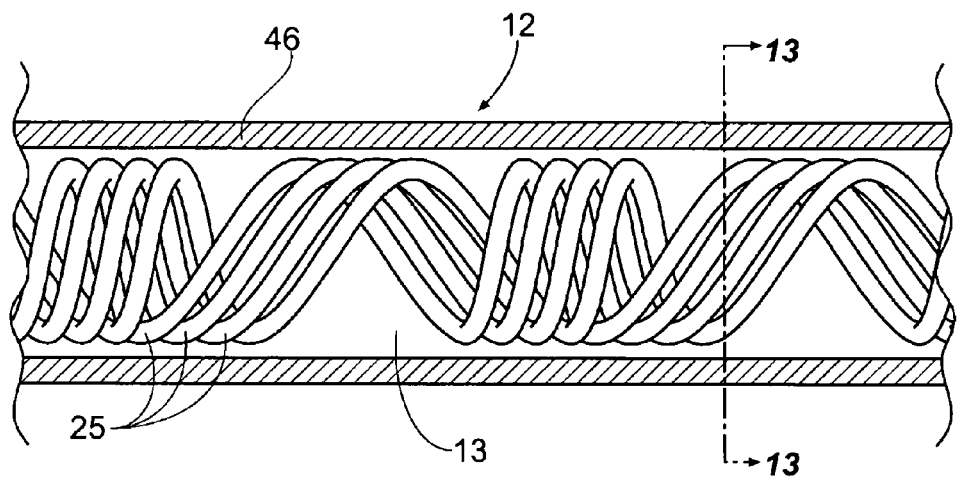
Figure 13:
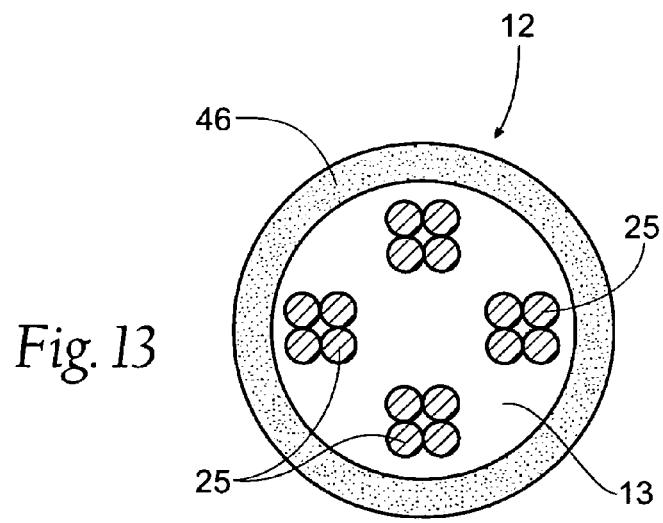
FIG. 13 is an end section view of the lead taken generally along line 13-13 in FIG. 11.

The coil's pitch can be constant, as FIG. 11 shows, or the coil's pitch can alternate from high to low spacing, to allow for flexibility in both compression and tension, as FIG. 12 shows. The tight pitch will allow for movement in tension, while the open pitch will allow for movement in compression.

Figure 22:
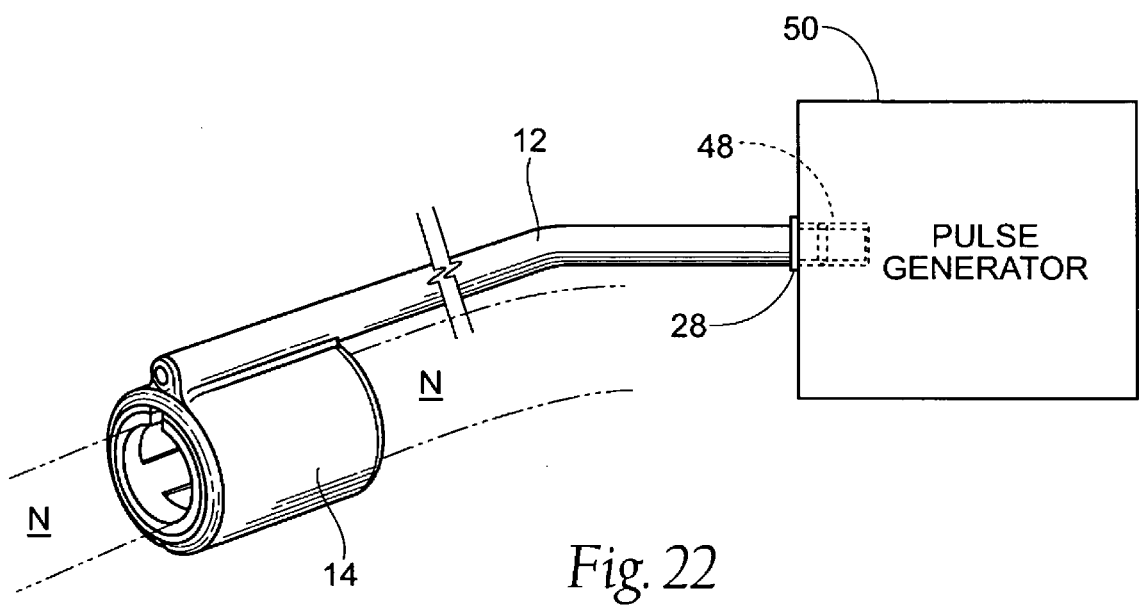
FIG. 22 is a perspective view of a molded nerve cuff as shown in FIG. 1, coupled to a pulse generator to deliver low frequency and/or high frequency waveforms, the system inducing action potentials in a targeted nerve (or nerves) to achieve a desired therapeutic result.

Implantable connectors may be similar in design and construction to the low-profile IS-1 connector system (per ISO 5841-3). A standard IS-1 or similar type connector 28 at the proximal end of the lead 12 provides electrical continuity and mechanical attachment to the mating connector 48 of an implantable pulse generator 50 (see FIG. 22). The lead 12 and connector 28 all may include provisions, i.e., lumen 13, for a guide wire that passes through these components and the length of the lead 12 to the distal end. Such a guide wire or stylet would allow the easy deployment of the lead 12 through an introducer.

Figure 14:
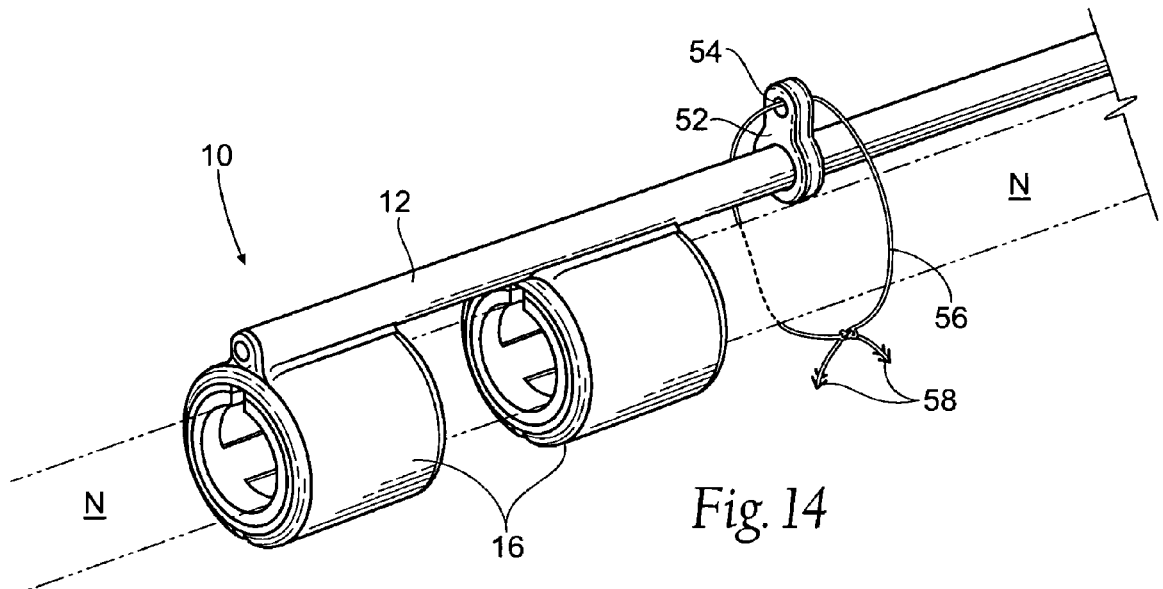
FIG. 14 is a perspective view of one embodiment of a securing means coupled to the lead of the nerve cuff shown in FIG. 2, the securing means including an aperture to allow a loop of suture to wrap loosely about the nerve to aid in maintaining the position of the implant system.
Figure 15:
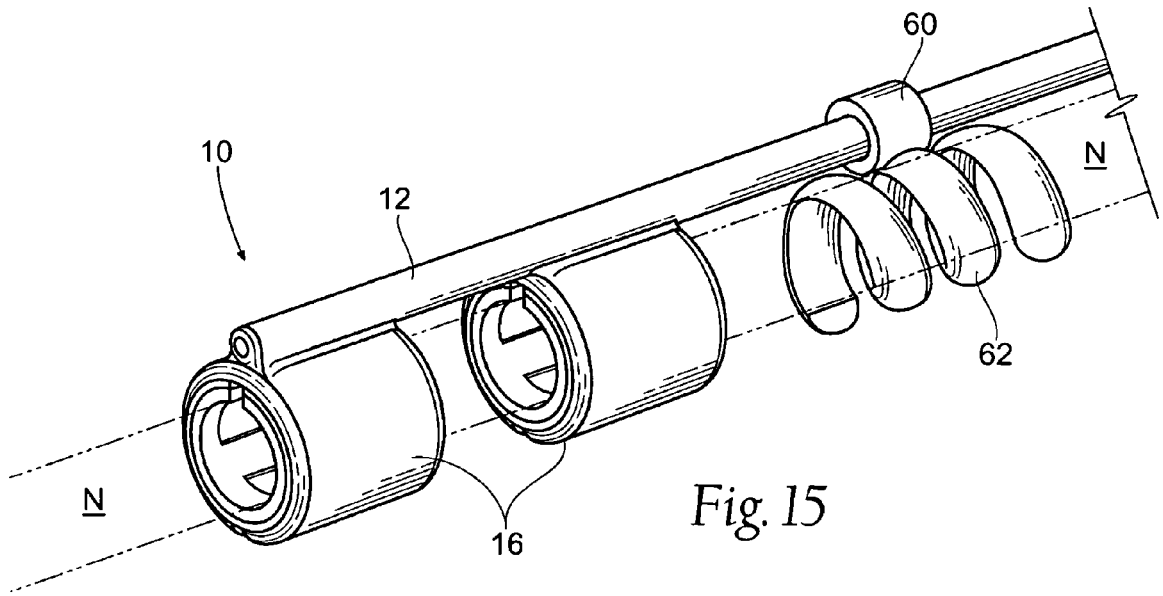
FIG. 15 is a perspective view of an additional embodiment of a securing means coupled to the lead of the nerve cuff shown in FIG. 2, the securing means including a spiraling element to wrap loosely about the nerve to aid in maintaining the position of the implant system.

As FIGS. 14 and 15 show, the system 10, being a molded component, desirably includes a molded or over-molded fastener means used to hold or anchor the distal portion of the lead 12 and cuff(s) 14, 16, to the target nerve N or other surrounding tissue. FIG. 14 shows a loop fastener 52. The fastener 52 is shown positioned over the lead 12, although it may also be an integral component of the lead. The fastener 52 includes an aperture 54 to allow a length of suture 56 to pass through the aperture 54 and then loop and be tied loosely around the nerve N, as shown. The suture 56 may also include one or more barbed elements 58 that may anchor into surrounding tissue to help secure the system 10 to the nerve, in addition to, or in place of tying. FIG. 15 shows a spiral fastener 60. The spiral fastener 60 is shown positioned over the lead 12, although it may also be an integral component of the lead. The fastener 60 includes a spiraling element 62 to wrap loosely around the nerve N, as shown. The spiraling element 62 may be less than one complete turn, or may be more than one complete turn (three turns are shown). The spiraling element 62 is opened, and then allowed to spiral around the nerve N. The spiral fastener 60 helps to hold the position of the system 10.

In a representative embodiment, the cuff(s) 14, 16, possess a minimum diameter (when in its normal molded condition) of as small as one mm, which makes it well suited for implantation about small nerves. The minimum diameter of the cuff can, of course, be molded to possess larger minimum diameters, to provide a family of implant systems 10 of different diameters that accommodate the range of diameters of human and animal nerves, from small to large.

Figure 16:
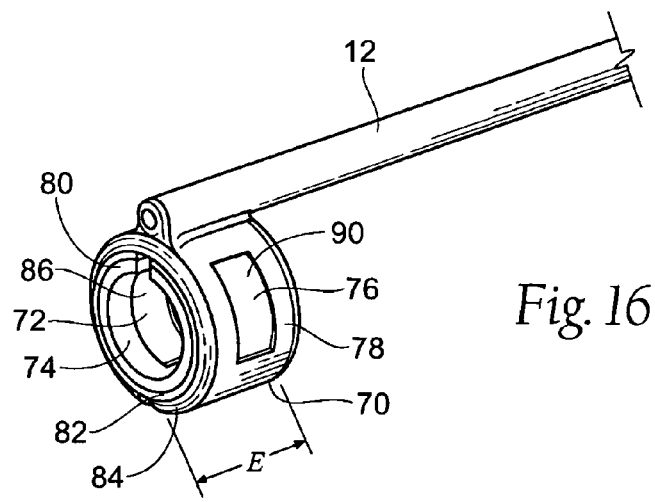
FIG. 16 is a perspective view of an additional embodiment of an implant system, the system including a lead and a molded split nerve cuff electrode implanted about a nerve, the nerve cuff including at least one electrode accessible at the inside surface of the cuff, and at least one electrode accessible at the outside surface of the cuff.

FIG. 16 shows an alternative embodiment of a split cuff. The alternative embodiment 70 incorporates all the features disclosed in the description of the cuffs 14, 16, and system 10, except the cuff 70 comprises the additional feature of including at least one electrode 72 accessible at the inside surface 74 of the cuff, and at least one electrode 76 accessible anywhere that is not at (i.e., away from) the inside surface of the cuff, e.g., at the outside surface of the cuff 78, as shown in FIG. 16. The electrode 76 could be positioned anywhere along the length of the lead 12 as well. This configuration allows the nerve cuff to have a shorter longitudinal length of "E", e.g., about 5 mm or less, and requires less length of the target nerve N to be exposed prior to placement of the cuff on the nerve. In the configuration described for cuffs 14 and 16, both the active and the return electrodes are exposed inside the cuff (see FIG. 1). The cuff 70 can be shorter because the return electrode 76 (typically the anode) is exposed on the outside of the cuff 70, (or elsewhere, such as on the lead) and the active electrode 72 (typically the cathode) is exposed on the inside of the cuff 70 near to or in contact with the target nerve N. This configuration causes the stimulus current to flow from the active electrode 72 through the nerve N and to the return electrode 76, i.e., the return electrode 76 is in electrical contact with the nerve N and/or electrode 72, but not in physical or intimate contact with the nerve N and/or electrode 72. The electrodes 72, 76, are shown positioned circumferentially around the cuff, to allow for the shorter longitudinal length.

The minimum longitudinal length of the cuff 70 is generally related to 1) how short it can be manufactured (manufacturing limit), and 2) how long it must be to activate the target fibers in the target nerve N (physiological limit). The physiological limit is determined by the internodal spacing of the target fibers of the target nerve N. Nerves are composed of individual fibers and groups of fibers, and the target fibers within a nerve will have a range of distances "d" between their nodes of Ranvier (d=internodal spacing). Though it is possible for the minimum longitudinal length of the cuff 70 to be less than d, it is desirable that the minimum longitudinal length of the cuff is greater than or equal to d. The internodal d is approximately 100D, where D is the diameter of the target fiber(s). For example, if the target fibers of the target nerve N have diameters ranging from about 15 µm to about 20 µm, then d, the internodal spacing, is about 1.5 mm to about 2.0 mm, so the minimum cuff longitudinal length should be about 2.0 mm.

The minimum current to activate the target nerve N will decrease (which makes the system more efficient) as the cuff gets longer. The typical internodal length ranges from about 1.0 µm to about 25 µm. To target small 1.0 µm diameter fibers (as in nerve blocking of c-fibers that transmit pain signals), the cuff could be as short as approximately 0.1 mm, but the difficulty in manufacturing and the increased fragileness of this short of a length of cuff make it less desirable. To activate 25 µm fibers, the desired minimum cuff length would be about 2.5 mm.

The width of the external electrode 76 (return or anode) on the outside 78 of the cuff 70 can be sized and configured differently based on whether the goal is to 1) prevent unwanted activation of nearby non-target nerves or 2) further minimize cuff length.

Unwanted activation of non-target nerves can be minimized by widening the width of the external electrode(s) 76 on the outside 78 of the cuff 70. The closer the edges of the return electrode 76 to the edges of the cuff, the more limited the current spread will be, thus limiting unwanted activation of non-target nerves. Also, the larger surface area of the return electrode will lower the current density outside the cuff, which again minimizes unwanted activation on non-target nerves.

Narrowing the return electrode 76, making its edges closer to the center of the outside 78 of the cuff, and farther from the edges of the cuff, will lengthen the distance of the current path and increase the current spread within the cuff. This will raise the potential inside the cuff 70 and facilitate depolarization of the target fibers.

Figure 17:
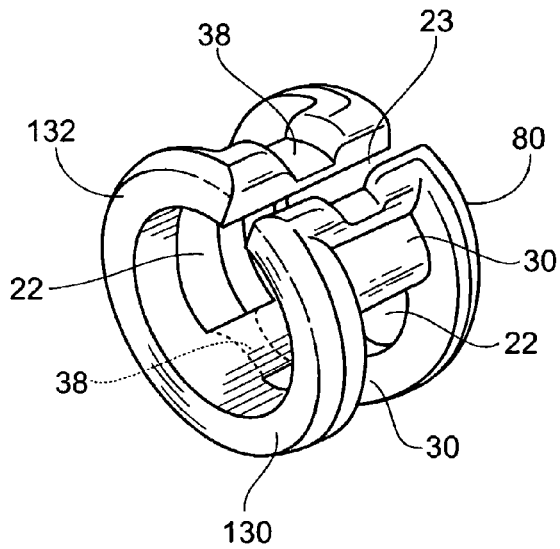
FIG. 17 is a perspective view of a split casing component having one or more circumferentially oriented frames and used to hold one or more electrodes in position, the casing used with the nerve cuff shown in FIG. 16.

The cuff 70 includes a split casing 80, insulating layer 82, and split cover tube 84, as described for cuffs 14 and 16. FIG. 17 shows the casing 80. As previously described, the casing 80 may be molded from a low durometer elastomer material, e.g., silicone or polyurethane, and includes an expansion portion 130 and a non-expansion portion 132, and one or more apertures or frames 22 to position and support a corresponding internal electrode 72. As can be seen, the casing 80 includes two frames 22, although more or less may be used. A longitudinal split 23 extending the length of the casing 80 provides an expandable access point to position the cuff 70 over the target nerve N.

Figure 18:
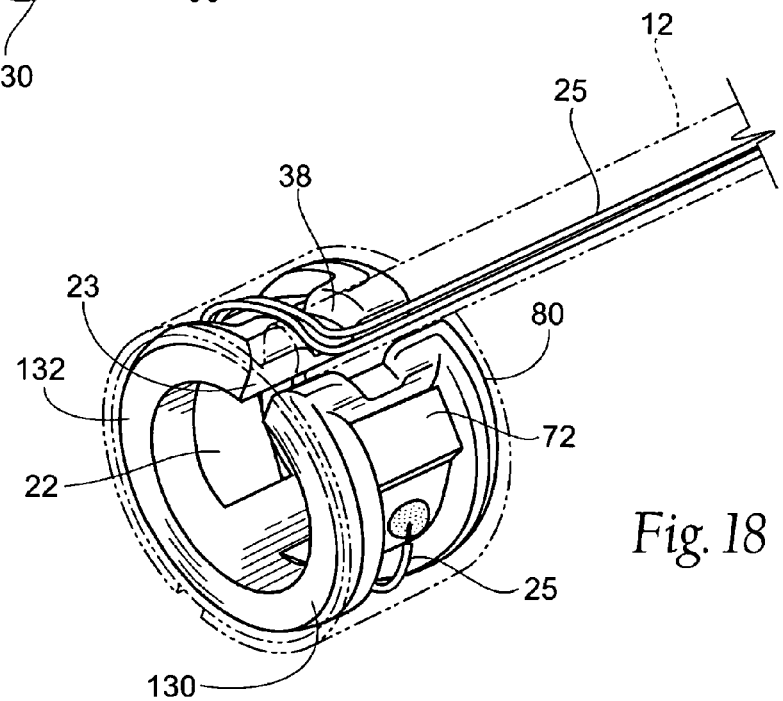
FIG. 18 is a perspective view of the split casing component shown in FIG. 17, having electrodes positioned in the frames and the lead wires extending from each electrode, through a channel, and into a lumen within the lead.

The casing 80 includes a single row of one or more circumferentially spaced frames 22 positioned around the circumference of the casing. Each frame 22 includes support structure 30 to allow the electrode 72 to be positioned within the frame 22 and extend through the casing 80 a predetermined amount. The tissue facing side 86 of the electrode 72 may extend beyond the inner surface 74 of the casing 80 or may be flush with the inner surface 74, or may be recessed within the frame 22, as shown in FIG. 16. Each frame also includes at least one channel 38 extending to an adjacent frame and the longitudinal split 23. The channel 38 is sized and configured to provide a path for the lead wire 25 to extend from the electrode 72 in a frame 22, around the casing 80, and into the lead 12 (see FIG. 18).

Figure 19:
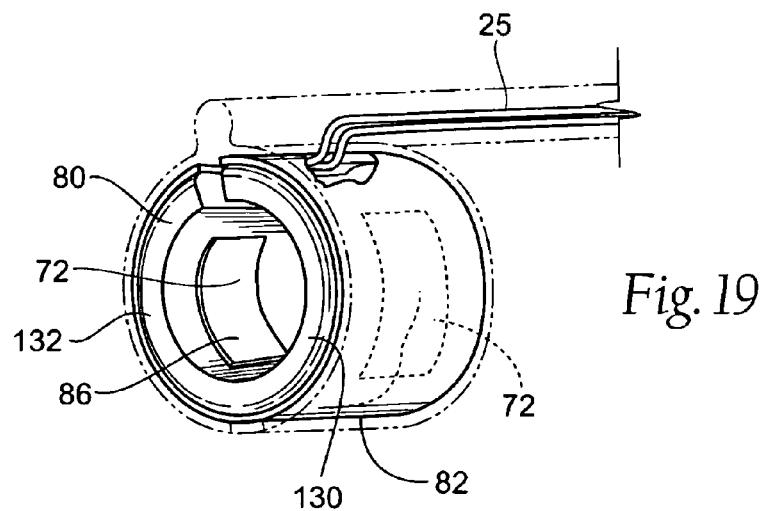
FIG. 19 is a perspective view of the split casing component shown in FIG. 18, and having electrodes positioned in the frames with the casing and electrodes covered with an insulating material, and the split cover tube shown in phantom.

With the electrodes 72 positioned within their respective frames 22, and the lead wires 25 positioned within a channel 38, a thin layer of insulating material 82 is positioned over the casing 80 (see FIG. 19). The insulating material 82 may be secured using known implantable bonding techniques (e.g., glued or bonded) to the casing 80. The lead wires 25 wrap around the casing starting on the casing expansion portion 130 and extend along the casing non-expansion portion 132 and under the insulating material until the lead wires 25 exit at the longitudinal split 23.

Figure 20:
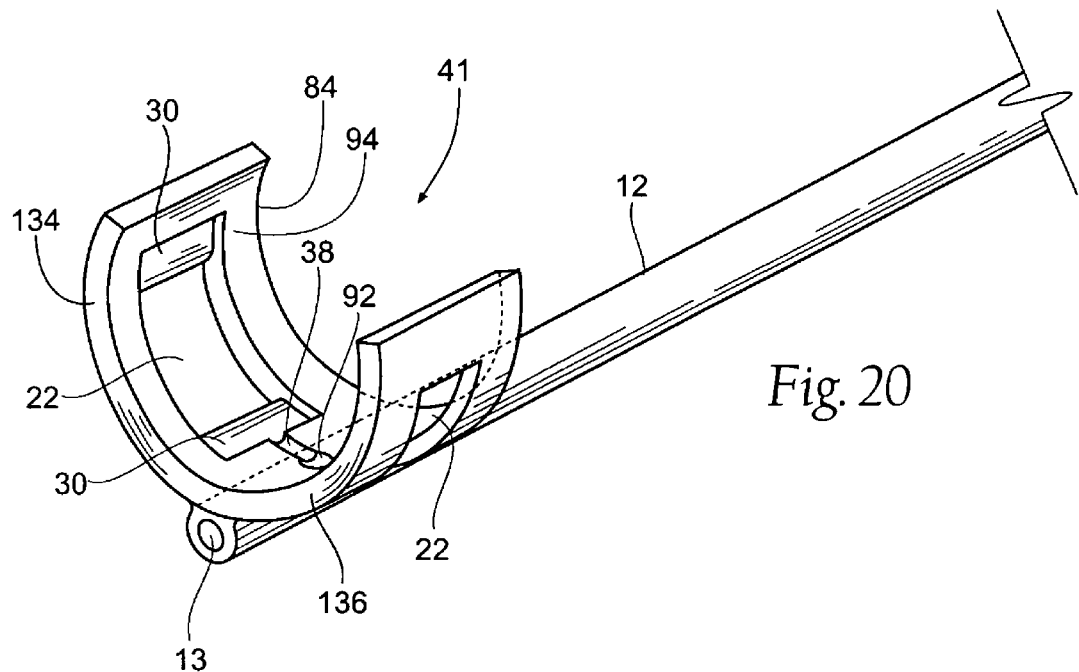
FIG. 20 is an interior perspective view of a split cover tube component used with the nerve cuff shown in FIG. 16, the cover tube including at least one frame used to hold one or more electrodes in position, the cover tube coupled to the distal end of the lead and used to hold the casing and insulating material in position.

As previously described for cuffs 14, 16, the casing 80, electrodes 72, and insulation 82, are positioned within the molded split cover tube 84 with the longitudinal split 23 positioned generally adjacent to the lead 12. As with the split casing 80, the split cover tube 84 also comprises an expansion portion 134 and a non-expansion portion 136. As previously described, the cover tube 84 may be molded from a low durometer elastomer material, e.g., silicone or polyurethane. As seen in FIG. 20, the molded cover tube 84 is coupled to or is integral with the distal portion of the lead 12, and includes a longitudinal split 41 extending the length of the cover tube. FIG. 20 shows the split 41 of the molded cover tube 84 spread open.

Figure 21:
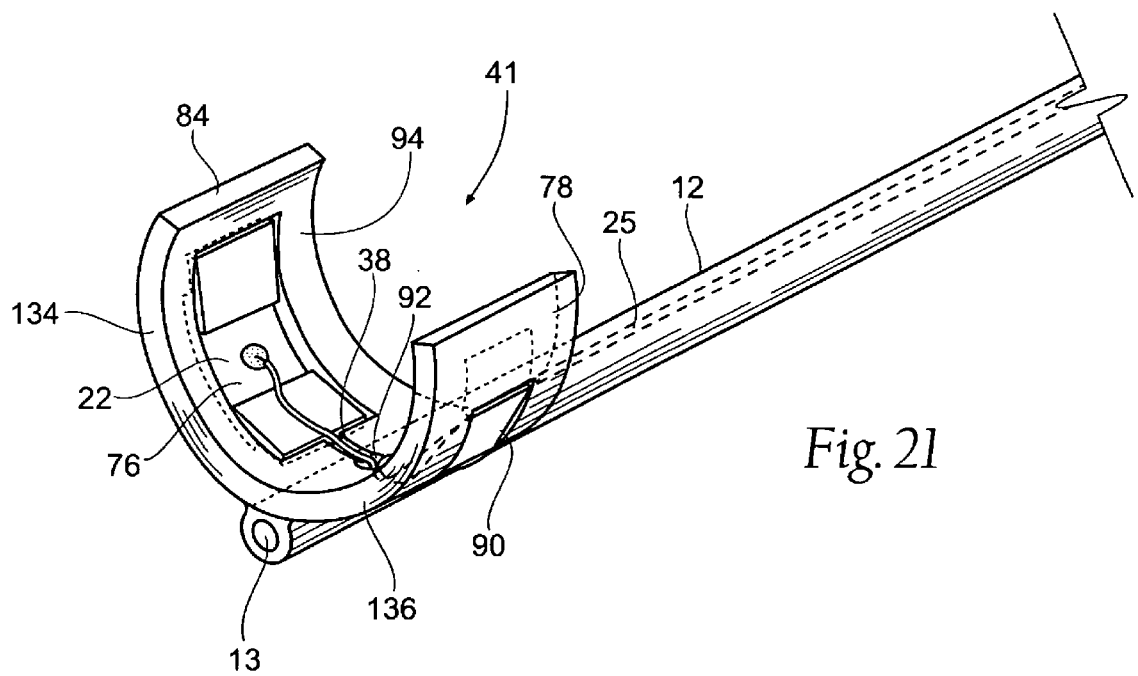
FIG. 21 is a perspective view of the split casing component shown in FIG. 20, having electrodes positioned in the frames and the lead wires extending from each electrode, through a channel, and into a lumen within the lead.

The cover tube 84 generally resembles the construction of the casing 80, except flipped inside out. The cover tube 80 includes one or more apertures or frames 22 to position and support a corresponding external electrode 76. As can be seen, the split cover tube 84 includes two frames 22, although more or less may be used. The longitudinal split 41 extending the length of the cover tube 84 provides an expandable access point to position the cuff 70 over the target nerve N. The cover tube 84 includes a single row of one or more circumferentially spaced apertures or frames 22 positioned around the circumference of the cover tube. Each frame 22 includes support structure 30 to allow the electrode 76 to be positioned within the frame 22 and extend through the cover tube 84 a predetermined amount (see FIG. 16). The cuff exterior facing side 90 of the electrode 76 may extend beyond the outer surface 78 of the cover tube 84 or may be flush with the outer surface 78, or may be recessed within the frame 22, as shown. Each frame also includes at least one channel 38 extending to an adjacent frame. The channel 38 is sized and configured to provide a path for the lead wire 25 to extend from the electrode 76 in a frame 22 and into the lead 12 (see FIG. 21).

At least one aperture 92 is positioned at the inner surface 94 of the cover tube 84, to allow the lead wire 25 to extend from the electrode 76 through a channel 38 and into the lumen 13. The lead wire 25 then extends to the connector 28 on the proximal end of the lead 12.

The insulation material 82 provides electrical insulation between the internal electrodes 72 and the external electrodes 76. The insulating material 82 also provides lubricity between the casing 80 and the cover tube 84 to allow the two surfaces to slide or adjust, i.e., open or close, during implantation and changes in nerve size.

II. Molded Nerve Cuff Assembly

The molded nerve cuffs as described above may be assembled in a number of different ways. In one embodiment, the cuff 14 is generally assembled by attaching (e.g., crimp, laser weld, resistance weld, etc.) an electrode 18 to the lead wire 25. The lead wires 25 may have already been positioned within the lumen 13 of the lead and routed out of the aperture 42. The electrode 18 is then placed into a frame 22 of the molded casing 20 and may be held in place with silicone (or other appropriate adhesive). The insulating material 24 may then be placed on top of the assembled casing 20 and electrode 18 and secured in place (i.e., silicone adhesive or other appropriate bonding techniques). The cover tube 26 may then be positioned over the assembled electrode 18, casing 20, and insulating material 24. The lead wire 25 may be gently pulled through the lead 12 to remove any slack. The cover tube 26 may then be secured (e.g., glued or bonded) in place along about half of its circumference, i.e., the cover tube non-expansion portion 126. The cover tube 26 is only partially secured to the insulating material to allow the non-secured portions to expand or open to allow the cuff to be implanted about a nerve. It is to be appreciated that this is but one embodiment of an assembly sequence, and that the process may be completed in alternative steps.

III. Implanting the Molded Nerve Cuff

Due to its mechanical and physical properties, the molded nerve cuffs shown and described above are, in use, well suited for placement about a peripheral nerve N to deliver a stimulation waveform. This is because the cuffs (i) may be sized and configured to reliably establish and maintain circumferential contact about a predetermined amount of the nerve periphery, (ii) exhibits a predictable and repeatable diameter vs. pressure curve, (iii) is adaptive to post-operative swelling, and (iv) resists the effects of translational and rotational forces to stay in place post-operatively.

In this use (see FIG. 22), the connector 28 at the proximal end of the lead 12 is coupled to a mating connector 48 of a stimulation pulse generator 50. The pulse generator 50 includes a circuit that generates electrical waveforms that are capable of stimulating the nerve N across its entire cross section or selectively over just a portion of the nerve cross section, e.g., using a predetermined low and/or high frequency waveforms.

A suitable implantable pulse generator 50 for use in the devices, systems, and method of the present invention is disclosed, for example, in U.S. patent application Ser. No. 11/517,056, filed Sep. 7, 2006, and entitled "Implantable Pulse Generator System and Methods for Providing Functional and/or Therapeutic Stimulation of Muscles and/or Nerves and/or Central Nervous System Tissue," which is incorporated herein by reference. Certain parameters of the stimulation waveform generated by the implantable pulse generator are programmable, preferably by means of an external programmer (not shown) in a conventional manner for implantable electrical medical devices.

A. Cuff Expansion Prior to Implantation

As described above and shown in the Figures, each of the nerve cuff embodiments includes a casing, a layer of insulating material over the casing, and a cover tube, defining a multi-layered molded cuff. As such, the following description will reference cuff 14, although it is to be appreciated that this description embodies each of the nerve cuff embodiments as well.

Nerve cuff 14 includes a casing longitudinal split 23 and a cover tube longitudinal split 41. The split casing 20 comprises an expansion portion 120 and a non-expansion portion 122, and the cover tube 26 comprises an expansion portion 124 and a non-expansion portion 126. Each split 23, 41 provides an access point to expand or open the cuff for implantation about a nerve. As shown in the Figures, the casing longitudinal split 23 is generally adjacent to the distal end of the lead 12, with the cover tube longitudinal split 41 positioned generally out of phase of the casing longitudinal split 23. The cover tube longitudinal split 41 can be positioned between about 90 degrees to about 270 degrees away from the casing longitudinal split 23 to provide sufficient closure of the cuff while allowing for changes in the size of the nerve. Desirably, the cover tube longitudinal split 41 is positioned about 180 degrees out of phase of the casing longitudinal split 23. It is to be appreciated that each split 23, 42 serves as an access point, and is not restricted to the positions as described.

Figure 23:
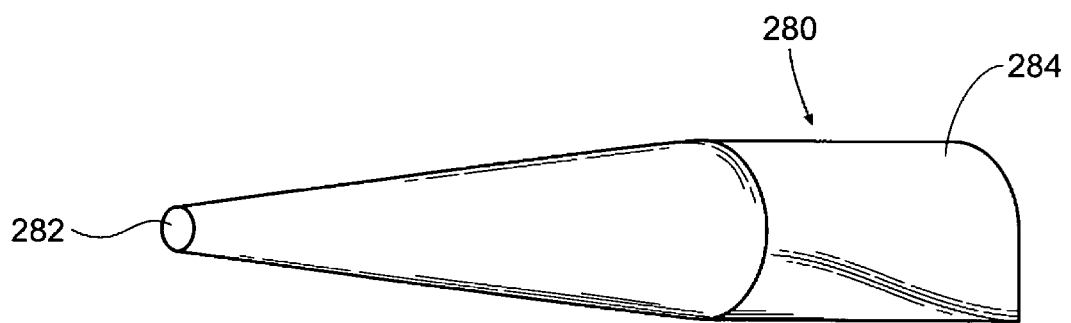
FIG. 23 is a perspective view of a conical or ramp shaped tool used to expand or spread open the nerve cuff for convenient grasping by an applicator tool.
Figure 24:
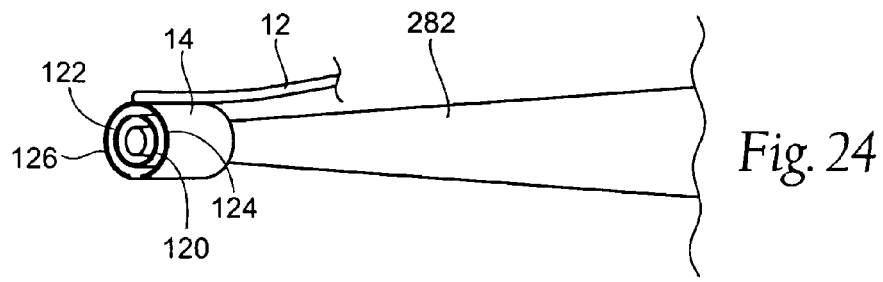
FIGS. 24 through 29 are perspective views showing the expansion process of the nerve cuff using the tool shown in FIG. 23.
Figure 25:
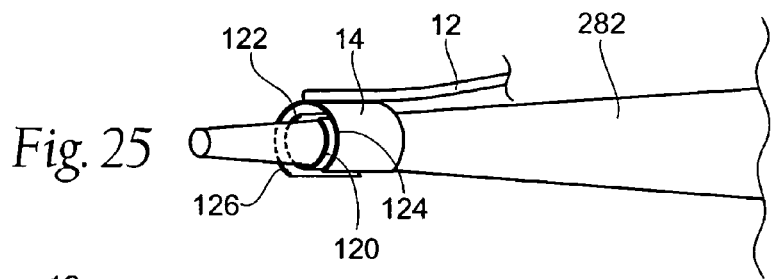
Figure 26:
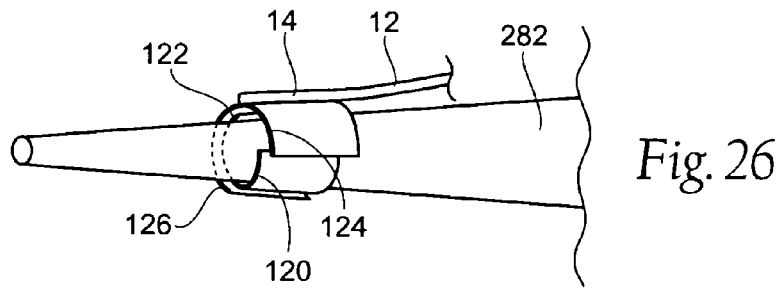
Figure 27:
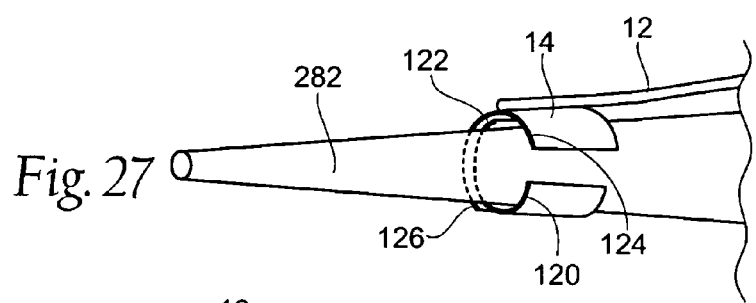
Figure 28:
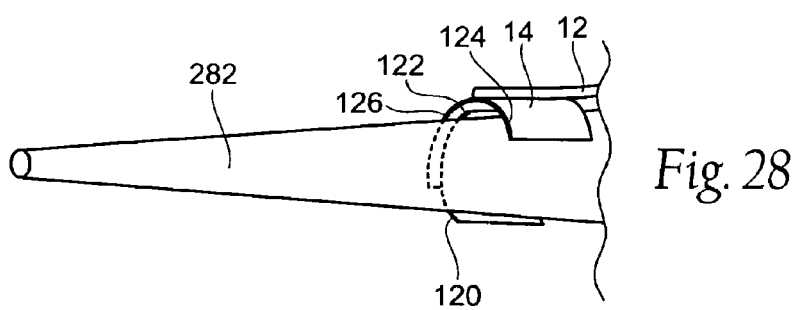
Figure 29:
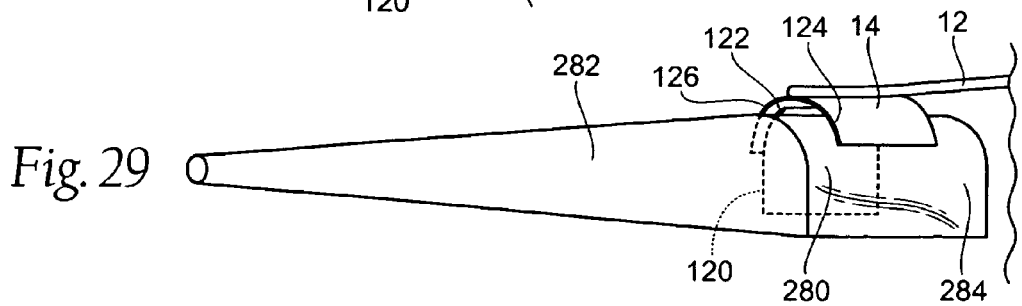

A tool 280 may be used to simplify the cuff expansion process. FIG. 23 shows a conically shaped expansion tool 280 that may be used to expand the nerve cuff so it may be positioned over the target nerve or conveniently grasped by or positioned on to an applicator tool to aid in the cuff implantation. The tool 280 includes a conical nose 282 on one end to expand the cuff and a base station 284 on the other end to maintain the expanded cuff configuration until the cuff is grasped for implantation or transferred to an applicator tool.

The cuff expansion is desirably accomplished immediately before placing the expanded cuff on a nerve or an applicator tool. To expand the cuff 14, the cuff is positioned on the tip of the conical nose 282 of the tool 280 and is gently pulled, or the tool pushed, to cause the casing expansion portion 120 and the cover tube expansion portion to open. FIGS. 24 to 29 show the process of the cuff 14 being slid along the length of the tool 280 until the split cuff 14 expands to a generally "U" shape at the base station 284. The expanded cuff 14 is then ready to be grasped for implantation or transferred to an applicator tool.

B. Implant Slider Applicator Tool

Figure 30A:
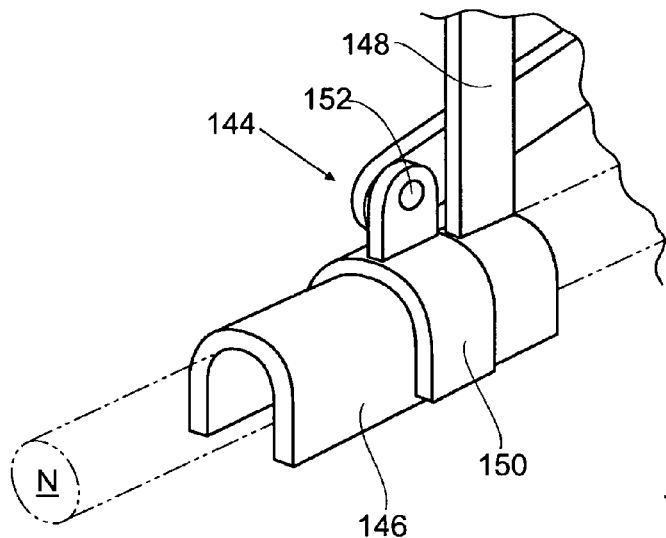
FIG. 30A is an applicator tool for placement of a molded nerve cuff of the type shown in FIG. 1 about a nerve, the applicator tool being shown before mounting of the nerve cuff with the cuff delivery mechanism in an aft condition.
Figure 30B:
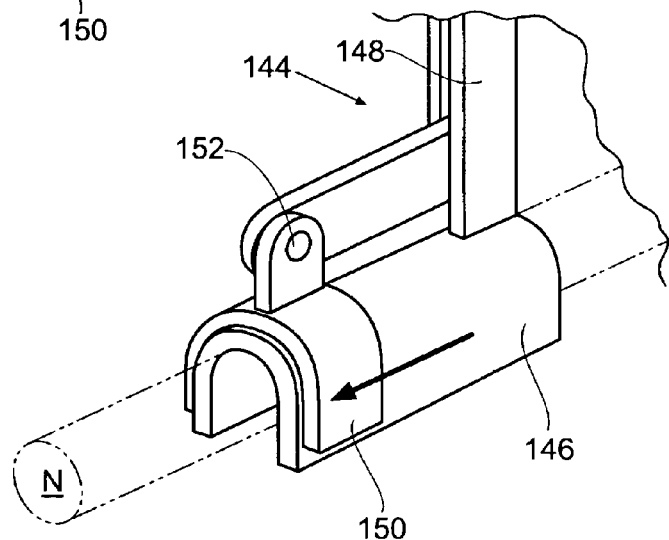
FIG. 30B is the applicator tool shown in FIG. 30A, the applicator tool being shown before mounting of the nerve cuff with the cuff delivery mechanism in a forward condition.
Figure 30C:
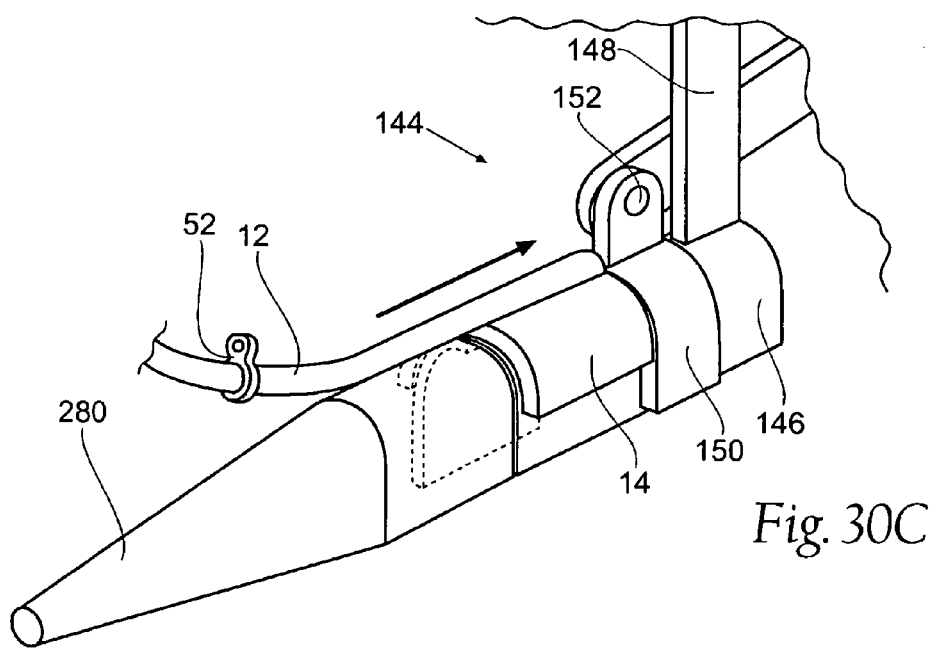
FIG. 30C is the applicator tool shown in FIG. 30A, with the nerve cuff mounted on the delivery tool, with the cuff delivery mechanism in an aft condition.

In one embodiment, the implantation of the cuff 14 can be facilitated by use of an applicator tool 144 (see FIGS. 30A to 30C). It is to be appreciated that the applicator tool 144 may be used for the implantation of cuffs 16 and 70 as well, and variations thereof. While tools of various configurations can be used, the applicator tool 144 shown in FIGS. 30A to 30C includes an applicator body 146 with a handle 148. As FIG. 30A shows, the applicator body 146 comprises an open ended, inverted trough for placement over a portion of a nerve N. As will be described later, the curvilinear form of the body 146 accommodates mounting of the cuff 14 in an expanded split condition.

The applicator tool 144 also includes a slider 150 carried on the body 146. The slider 150 moves along the axis of the body 146 between an aft position (FIG. 30A) and a forward position (FIG. 30B). A scissors-type linkage 152 is coupled to the handle 148 so an operator can easily affect movement of the slider 150 fore and aft. Opening the linkage 152 moves the slider 150 aft (see FIG. 30A); closing the linkage 152 moves the slider forward (see FIG. 30B).

Figure 31A:
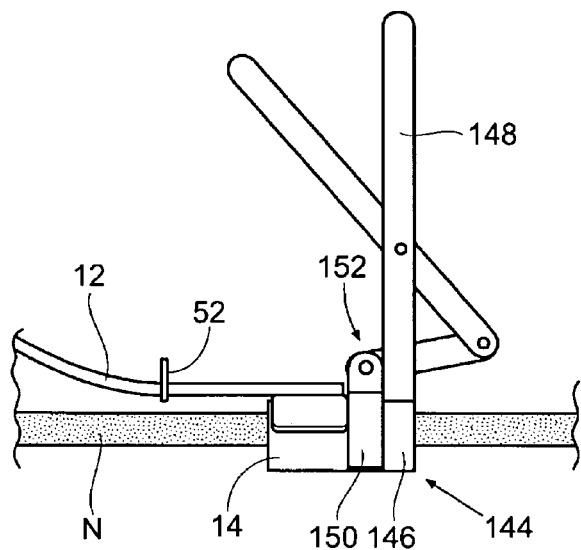
FIG. 31A is a side view of the applicator tool shown in FIG. 30C, with the nerve cuff mounted and the cuff delivery mechanism in an aft condition, ready to implant the electrode about a nerve.

The inverted trough shape of the applicator body 146 is sized and configured so that, when the slider 150 is in is aft position, the split cuff 14 can be expanded and mounted on the body 146 forward of the slider 150, as FIG. 30C shows. This is desirably accomplished immediately before placing the applicator tool 144 in the targeted position on the nerve N, which is shown in FIG. 31A.

Figure 31B:
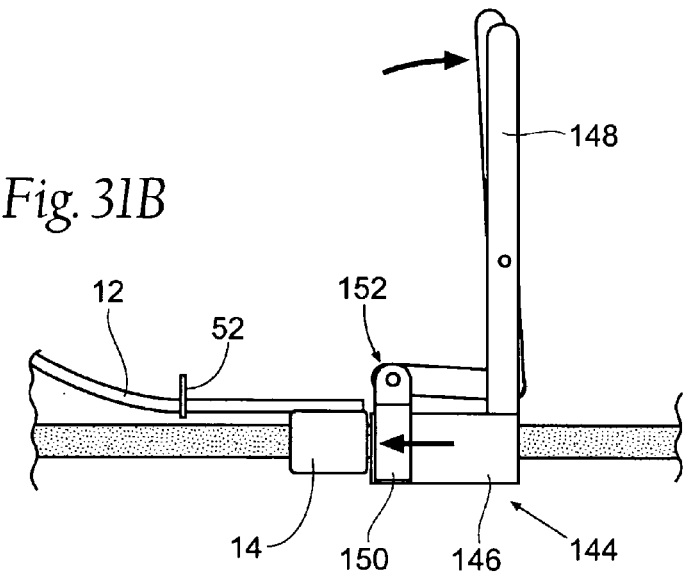
FIG. 31B is a side view of the applicator tool shown in FIG. 31A, with the cuff delivery mechanism translated to a forward condition to implant the cuff about a nerve.
Figure 31C:
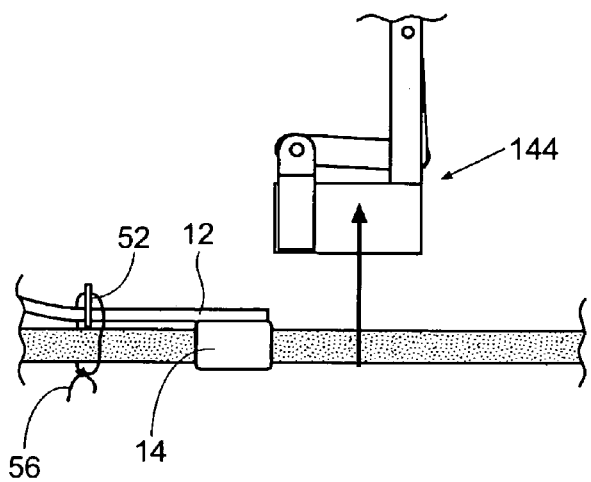
FIG. 31C is a side view of the applicator tool shown in FIG. 31A, after implantation of the nerve cuff about a nerve and withdrawal of the application tool from the nerve.

Closing the linkage 152 (as FIG. 31B shows), moves the slider 150 forward. The slider pushes against the cuff 14 and ultimately ejects the cuff 14 from the applicator body 146 onto the nerve N (as FIG. 31B shows). Free of the trough-shaped applicator body 146, the elastic memory of the molded cuff 14 causes it to wrap about the nerve N, and assume the configuration as FIG. 1 shows. The applicator tool 144 can now be removed from the nerve N, leaving the system 10 implanted about the nerve (as FIG. 31C shows).

The expansion tool 280 and the applicator tool 144 can be formed of a metal or plastic material, and are desirably supplied as part of a sterile kit with the system 10 as single-use devices. Desirably, the tool 144 is molded from snap together medical grade plastic parts (e.g., polystyrene). It is to be appreciated that the expansion tool 280 and the applicator tool 144 could be an integrated tool (see FIG. 30C) with the expansion tool 280 portion being snapped off or disconnected from the application tool 144 prior to implantation.

The applicator tool 144 makes possible a straightforward and reliable placement of the cuffs 14, 16, 70, and their equivalents, into humans and animals, e.g., installation in vivo desirably is accomplished in one minute or less.

C. Implant Pressure Applicator Tool

Figure 32:
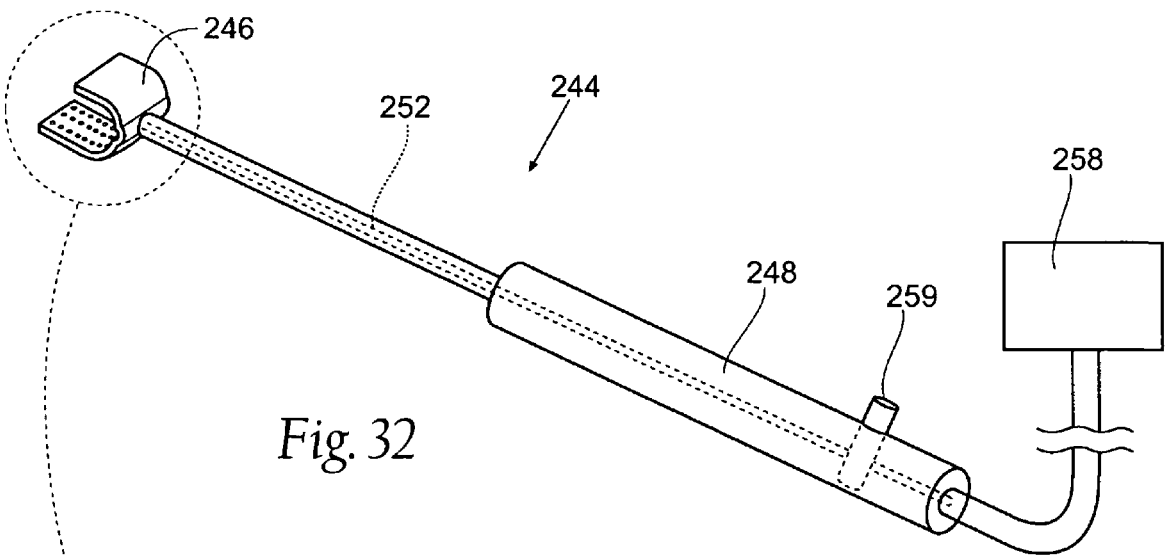
FIG. 32 is a perspective view of an applicator tool for placement of a molded nerve cuff of the type shown in FIG. 1 about a nerve, the applicator tool being shown before mounting of the cuff and attached to a vacuum pressure source.
Figure 33:
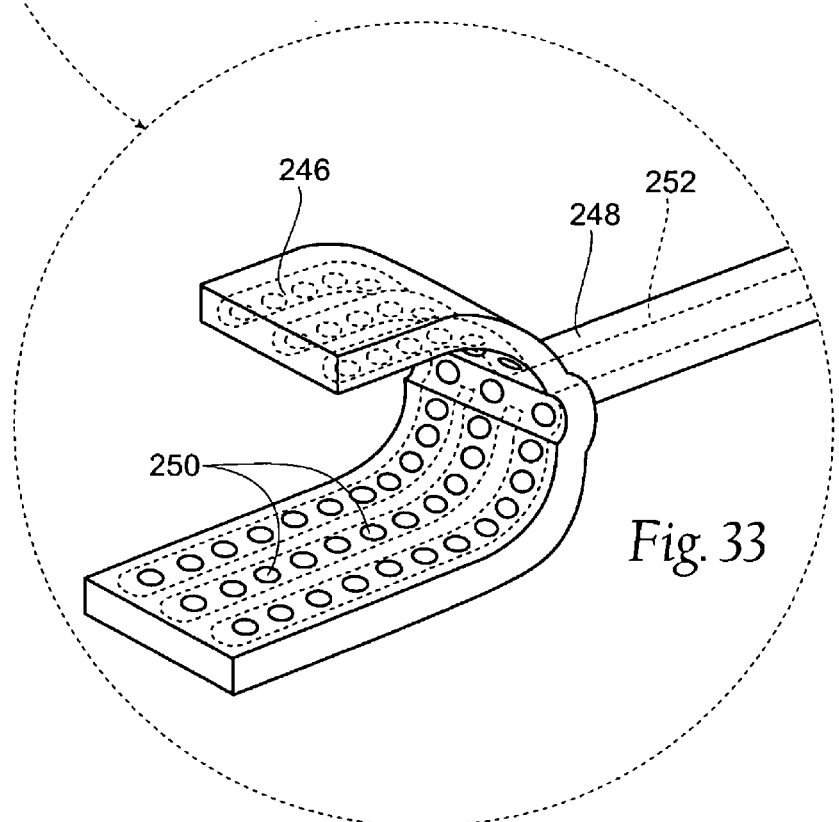
FIG. 33 is a detailed view of the "U" shaped distal end of the applicator tool shown in FIG. 32.

In an additional embodiment, the implantation of the cuff 14 can be facilitated by use of an applicator tool 244 (see FIGS. 32 and 33). It is to be appreciated that the applicator tool 244 may be used for the implantation of cuffs 16 and 70 as well, and variations thereof. While tools of various configurations can be used, the applicator tool 244 shown in FIGS. 32 and 33 includes a handle 248 having an open ended, inverted trough or "U" shape grasping distal end 246 to embrace the exterior surface 45 of the cuff 14 and to hold the cuff in the open "U" shape for placement over a portion of a nerve N. The distal end 246 allows the cuff 14 to be implanted without the applicator tool 244 ever touching the target nerve N. In addition, the distal end 246 of the applicator tool 244 is sized and configured to be just slightly wider than the cuff being implanted, which in turn requires only a very small accessible space on the nerve necessary to implant the cuff. As is described below, the generally "U" shaped form of the distal end 246 accommodates mounting of the cuff 14 in an expanded split condition.

The distal end 246 of the applicator tool 244 includes a plurality of ports 250 that are in fluid communication with at least one lumen 252 extending within the handle 248 of the applicator tool 244. A vacuum is applied to the lumen 252 that causes the soft body of the cuff 14 to be held open within the distal end 246 as the cuff is saddled onto the nerve N.

Figure 34:
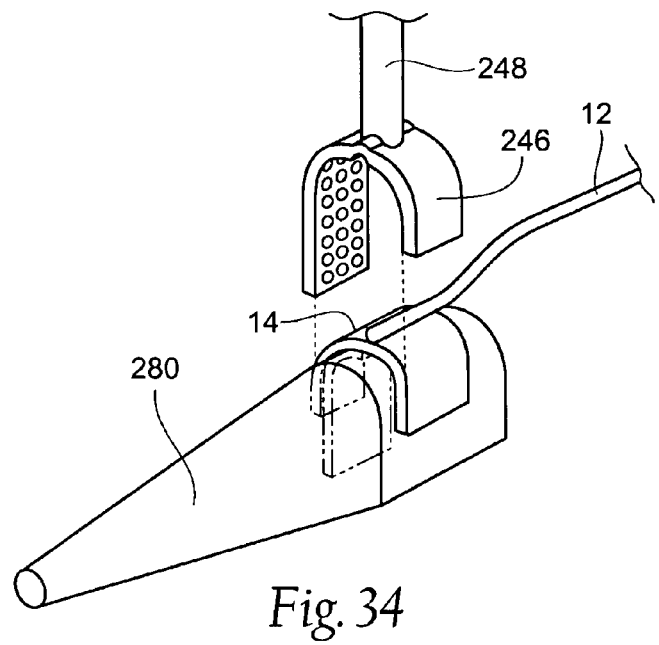
FIG. 34 is a partial view of the applicator tool shown in FIG. 32, the applicator tool in a position to grasp the nerve cuff positioned on the expansion tool.
Figure 35:
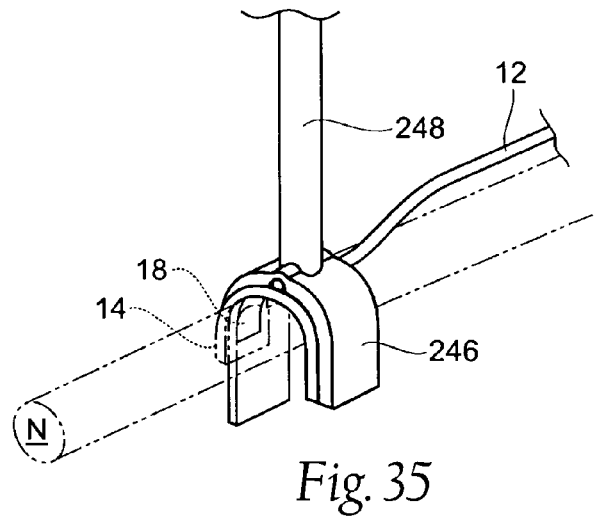
FIG. 35 is a perspective view of the applicator tool shown in FIG. 32, with the nerve cuff mounted and ready to be released from the delivery tool and implanted about a nerve.

As previously described, the expansion tool 280 may be used to shape the cuff electrode so it may be conveniently grasped by the applicator tool 244 (see FIG. 34). This is desirably accomplished immediately before placing the applicator tool 244 in the targeted position on the nerve N, which is shown in FIG. 35. The applicator tool 244 is positioned over the cuff 14 and a vacuum is applied through the applicator tool. The vacuum pressure holds the cuff 14 in place within the distal end 246 of the applicator tool 244.

In the embodiment shown in FIGS. 32 and 33, a lumen 252 extends the length of the handle 248 and is coupled to an external vacuum source 258. The vacuum pressure may be released via the external vacuum source 258 and/or vacuum release means on the handle 259. It is to be appreciated that the applicator tool 244 may include a variety of vacuum release means, such as vent button or valve release, for example.

Figure 36:
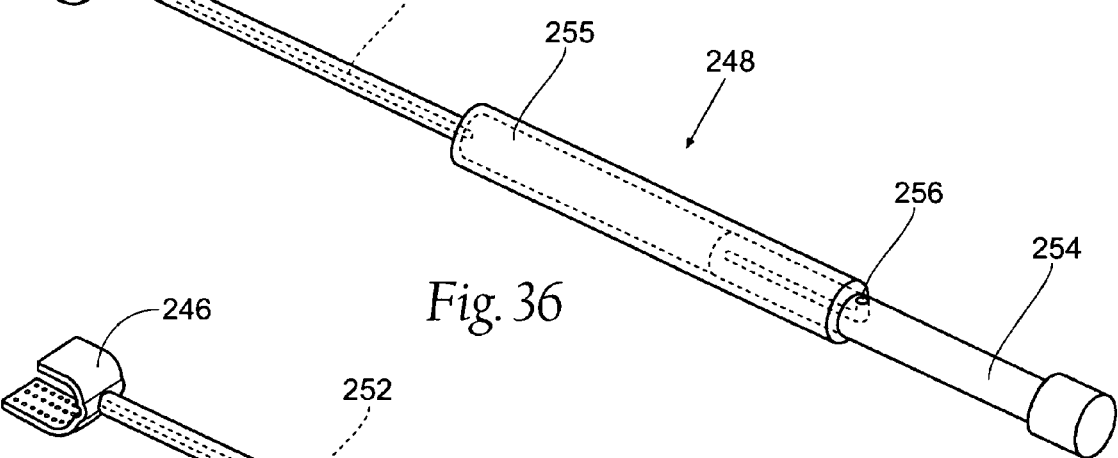
FIGS. 36 and 37 are perspective views of an alternative embodiment of the applicator tool shown in FIG. 32, the applicator tool having a plunger and barrel configuration for vacuum pressure generation.
Figure 37:
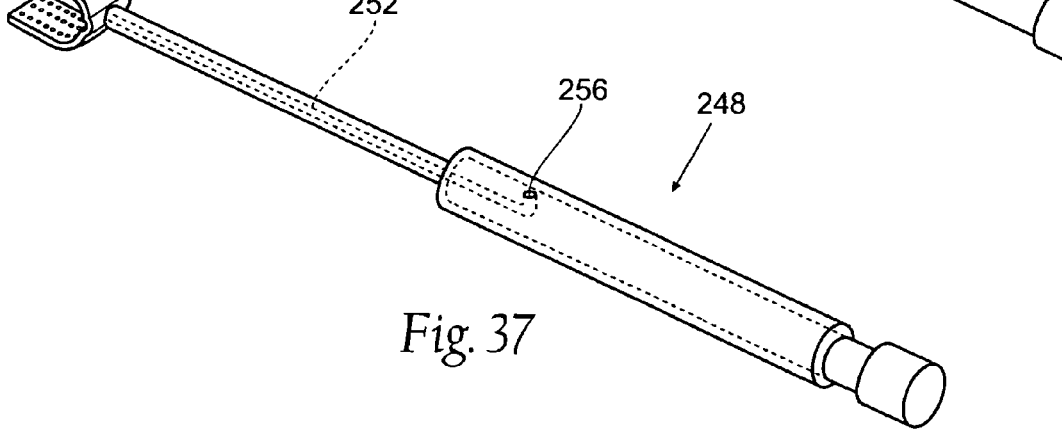

In an alternative embodiment shown in FIGS. 36 and 37, the handle 248 may include a plunger 254 sealably fitted within a barrel 255. When the plunger 254 is partially withdrawn from the barrel 255, a vacuum pressure is created within the barrel and lumen 252 sufficient to cause the soft body of the cuff to be held within the distal end 246 as the cuff electrode 14 is saddled onto the nerve N. The clinician may either push the plunger 254 back into the barrel 255, reducing or eliminating the vacuum pressure and allowing the cuff electrode to curl around the target nerve N, or continue to pull the plunger 254 until a vent 256 is exposed, releasing the vacuum pressure. Free of the open "U" shaped distal end 246, the elastic memory of the molded cuff 14 causes it to coil about the nerve N, and assume the configuration as FIG. 1 shows. The applicator tool 244 can now be removed from the nerve N, leaving the cuff electrode 14 implanted about the nerve N.

The applicator tool 244 can be formed of a metal or plastic material. Desirably, the tool 244 is molded from snap together medical grade plastic parts (e.g., polystyrene), and is supplied as part of a sterile kit with the cuff electrode 14 and the expansion tool 280 as single-use devices.

The applicator tool 244 makes possible a straightforward and reliable placement of the cuff electrode 14 into humans and animals, e.g., installation in vivo desirably is accomplished in one minute or less.

IV. Representative Indications

There are various conditions and diseases where use of the system 10 to apply a stimulus waveform therapy may be indicated. Representative examples will be described for the purpose of illustration.

A. Sexual Function Restoration

Neuromodulation stimulation has been used for the treatment of sexual dysfunction, which affects both men and women. A wide range of options exist for the restoration of sexual function. Treatments include everything from medications, simple mechanical devices, psychological counseling, external stimulators, and surgically implanted devices.

The nervous system affecting the genitalia of both the male and female are similar. One form of male sexual dysfunction is know as Erectile Dysfunction (ED), and is often referred to as "impotency." There are some common diseases such as diabetes, Peyronie's disease, heart disease, and prostate cancer that are associated with impotency or have treatments that may cause impotency. And in some cases the cause may be psychological.

Persons with erectile dysfunction are unable to achieve penile erection due to a variety of reasons, such as either insufficient arterial blood flow or insufficient venous occlusion or both. Normal reflex erection coordinates dilation of penile blood vessels, augmenting vascular filling, and venous occlusion, preventing leakage and increasing penile stiffness.

Electrical stimulation of the nerves affecting the genitalia has been used for sexual function restoration. Electrical stimulation of one or more target nerves N, either alone or in combination, activates spinal circuitry that coordinates efferent activity in the cavernous nerve (CN), increasing filling via dilation of penile arteries, and efferent activity in the pudendal nerve (PN), preventing leakage via occlusion of penile veins, producing a sustained reflex erection. The target nerves N may include the dorsal nerve of the penis (DNP), the cavernous nerve (CN), and/or the pudendal nerve (PN).

B. Bladder Dysfunction

Bladder dysfunctions of a variety of forms affect a large population. For example, about thirteen million Americans suffer from various types of urinary incontinence. Various treatment modalities for urinary incontinence have been developed. These modalities typically involve drugs, surgery, or both. Disposable pads can also used, not to treat the disorder, but to deal with its consequences.

Damage to the bladder, urethra, periurethral muscles and sphincters, nerves, and accessory organs can be experienced by women during childbirth or hysterectomy. This damage can lead to urinary incontinence. Prostate problems can lead to urinary incontinence in men. The number of people suffering from urinary incontinence is on the rise as the population ages.

Neurostimulation of a variety of nerves in the pelvic region has been used in an attempt to treat urinary incontinence. It has been discovered that electrical stimulation current delivered to one or both of the left and right branches of the dorsal genital nerves, present near the clitoris in a female and near the base of the penis of a male, may be effective in treating urinary incontinence.

C. Cerebral Palsy Cerebral Palsy (CP) is a condition that includes a broad category of symptoms that involve impairment of motor control due to central nervous system (CNS) injury occurring around the time of birth.

There is no standard therapy that works for all patients or all symptoms. Drugs can be used to control seizures and muscle spasms, and special braces can compensate for muscle imbalance. Surgery and mechanical aids may help to overcome some impairments; counseling for emotional and psychological needs, and physical, occupational, speech, and behavioral therapy may also be employed.

One dominant symptom of CP is spasticity of muscles. If the spasticity is not controlled, then contractures develop. Once this happens, the muscles are permanently shortened and function is compromised. By implanting bilateral two channel high frequency nerve blocks, one on each obdurator nerve and the other on each tibial nerve, action potential conduction to the gluteals and the adductors can be blocked at night. The nerve block can be turned off during the day and the patient can still have volitional control over the muscles.

A more advanced application of this technology would be to monitor EMG signals on the nerve or muscle and automatically detect the start of a spasm. Once detected, the nerve block would be applied to the related muscles to prevent the spasm.

One of the most effective treatments today for spasticity in CP patients is the Baclofen pump. This provides general systemic relief to the CP patient. However, it needs to be refilled every two to four months and has to be carefully set up. Also, the fact that it is systemic means that it may have unwanted side effects.

The United Cerebral Palsy Society estimates incidence in the US in 2002 to be 9500; prevalence is 550,000. They did note that incidence has been dropping due to better neo and post natal care. Since CP patients are typically identified as children, the parents (and otshers) have to consider a lifetime of care options.

D. Other CNS Conditions

Other conditions that result in spasticity are Multiple Sclerosis (MS), Stroke, Spinal Cord injury and other CNS conditions. Stroke, with a high incidence and prevalence (750,000/yr and 5 million), is a possible target application but stroke patients, with a much older average age, may not be as likely to consider surgery as a treatment alternative. However, MS patients are younger and more active and might be a suitable target population. A 2002 study estimated that approximately 200,000 to 350,000 Americans suffer from MS, with an incidence of 10,000 people per year. Older studies suggest that it affects about 1.1 million people worldwide. The incidence appears to be increasing in women.

E. Phantom Pain in Amputations

Neuromas (and phantom pain in amputations) are an enlargement of the sheath of the nerve. Neuromas sometimes develop after amputation of a limb. They are frequently intractable and very painful.

It is estimated that there are 350,000 amputees living in the United States, with approximately 135,000 new amputations occurring each year. The number of amputees worldwide is not currently tracked by any organization. In the United States, the most common causes of amputation of the lower extremity are disease (70%), trauma (22%) congenital or birth defects (4%) and tumors (4%). Upper extremity amputation is usually due to trauma or birth defect with disease not as great of a contributing factor.

In one form or another pain is experienced by virtually 100% of people following an amputation. Immediate post-op pain is the pain experienced after any surgical procedure where skin, muscle, bone and nerves are cut. Essentially everyone experiences some degree of post-op pain following an amputation. It can usually be controlled with pain medication and subsides fairly rapidly as swelling goes down, tissues begin to heal, and the wound stabilizes.

But long term pain in the residual limb significantly affects as many as 40% of the amputees more than a year after amputation. Neuromas are only one of the underlying causes of post-amputation pain.

The use of the high frequency nerve block would address the some of the intractable chronic pain following an amputation by blocking the action potentials in the afferent nerves.

F. Trigeminal Neuralgia

Trigeminal Neuralgia causes severe intractable episodes of facial pain that are poorly controlled by medication and often chronic in nature. Last resort treatment often includes transection of the trigeminal nerve which relieves the pain but also causes paralysis of some of the muscles in the face.

The use of the high frequency nerve block would address the same type of the intractable chronic pain following an amputation by blocking the action potentials in the afferent nerves. A reversible nerve block offers a superior solution by blocking the pain as needed and reversing the block when not needed.

G. Sleep Apnea

Sleep apnea is a sleeping disorder where the person experiences shallow breathing or stops breathing altogether many times during their sleep. This can occur hundreds of times in a night and occurrences can last for several seconds or longer. Sleep apnea causes a disruption in the quality and quantity of sleep.

Sleep apnea generally occurs in three forms. They include obstructive, central, and mixed. Obstructive sleep apnea (OSA) occurs when the airway passage is physically blocked by the soft tissues in and around the throat area. During sleep, these soft tissues collapse and block the airway passage, causing the person to go without breathing until their brain wakens them so they can resume breathing. It is estimated that approximately 12 million people in the U.S. suffer from OSA. In central sleep apnea, the brain is the cause, not the savior. The airway passage remains open but the brain fails to provide signals to the body to breath. Mixed sleep apnea is a combination of obstructive and central sleep apnea.

Sleep apnea occurs in both children and adults, and has been linked to many unwanted consequences. High blood pressure, cardiovascular disease, weight gain, depression, headaches, memory problems, depression, and sleepiness during the day are all potential problems associated with sleep apnea.

Stimulation of muscles and nerves in humans during sleep has been attempted to improve the upper airway patency and reduce episodes of OSA. For example, electrical stimulation of the hypoglossal nerve affects the genioglossus and the geniohyoid muscles, which are the primary muscles involved in dilating the upper airway. Contraction of the genioglossus muscle provides tongue protrusion which in turn, dilates the airways.

1. The Anatomic Structures

Figure 38:
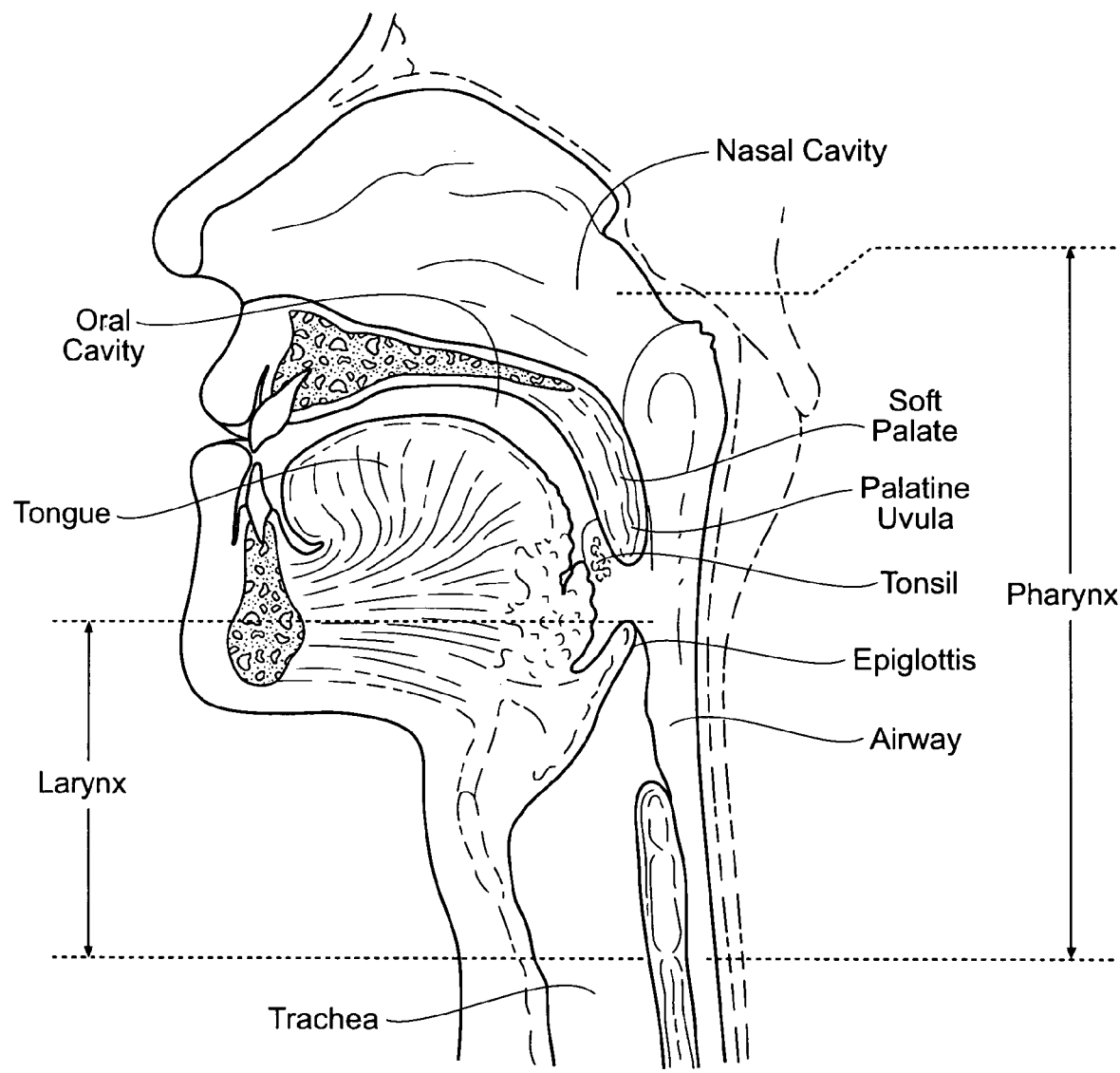
FIG. 38 is an anatomic cross sectional view showing the mouth and throat region of a human.

The structure of the throat generally comprises two main components, the pharynx and the larynx, as shown in FIG. 38. The pharynx is the tubal part of the throat that connects the nasal and oral cavities. The opening of the pharynx is visible when the mouth is open, and exposes the anterior of the pharynx, which is connected to the nasal cavity and the oral cavity between the soft palate and the root of the tongue. The wall of the pharynx is composed of layers of striated muscle. The soft palate comprises a muscular flap that separates the oral cavity from the pharynx when swallowing or speaking. The uvula is a small cone-shaped mass of tissue extending down from the soft palate.

The larynx, branching off of the pharynx, is the airway communicating with the trachea. The larynx is the boundary between the upper airway and the lower airway and includes the epiglottis. The epiglottis adjusts to control breathing and to protect the airway. The epiglottis is a flap of cartilage that lies behind the tongue and in front of the entrance to the larynx. When at rest, or when breathing, the epiglottis is upright and allows air to pass through the larynx and into the rest of the respiratory system. During swallowing, the epiglottis folds back to cover the entrance to the larynx, preventing food and drink from entering the airway.

Figure 39:
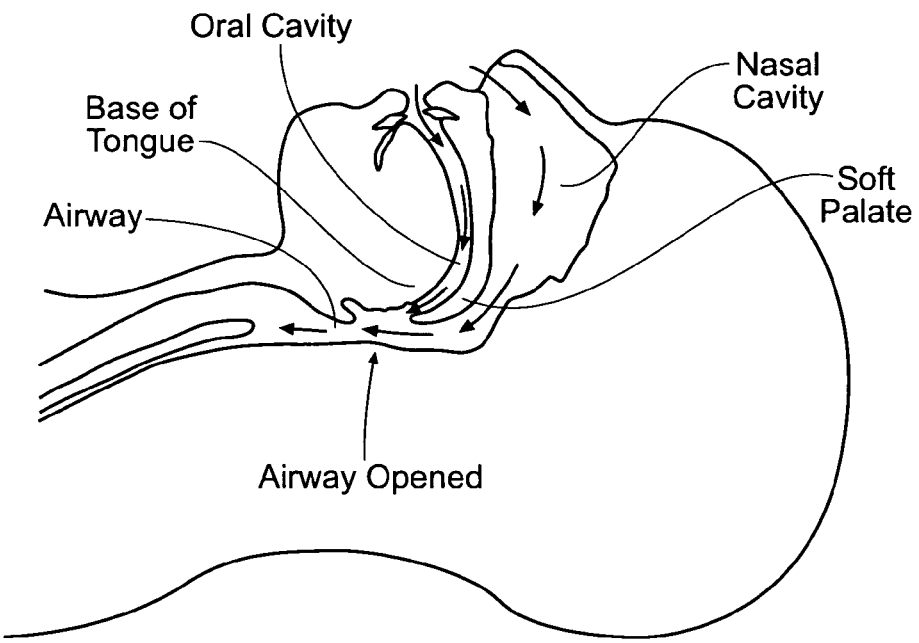
FIG. 39 is an anatomic view of the head and neck region of a human and showing an open airway and normal positioning of soft tissues of the throat.
Figure 40:
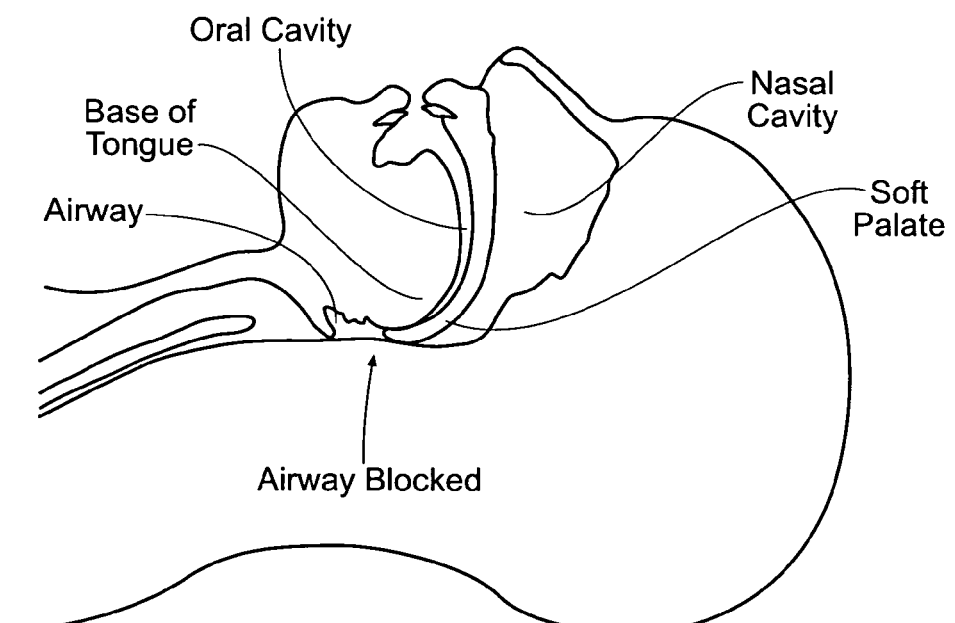
FIG. 40 is an anatomic view of the head and neck region of a human and showing a blocked airway and obstructive positioning of soft tissues of the throat.

Obstructive sleep apnea occurs when the muscles that support the soft tissues in the throat relax. These soft tissues include the tongue, soft palate, uvula, and tonsils, for example. When these muscles relax, the soft tissues collapse causing the airway to narrow or close, and breathing is momentarily cut off. FIG. 39 shows a normal open airway, and FIG. 40 shows an obstructed airway, representative of OSA. As seen in FIG. 40, the tongue and soft palate relax, causing them to drop down and restrict or close off the airway.

Figure 41:
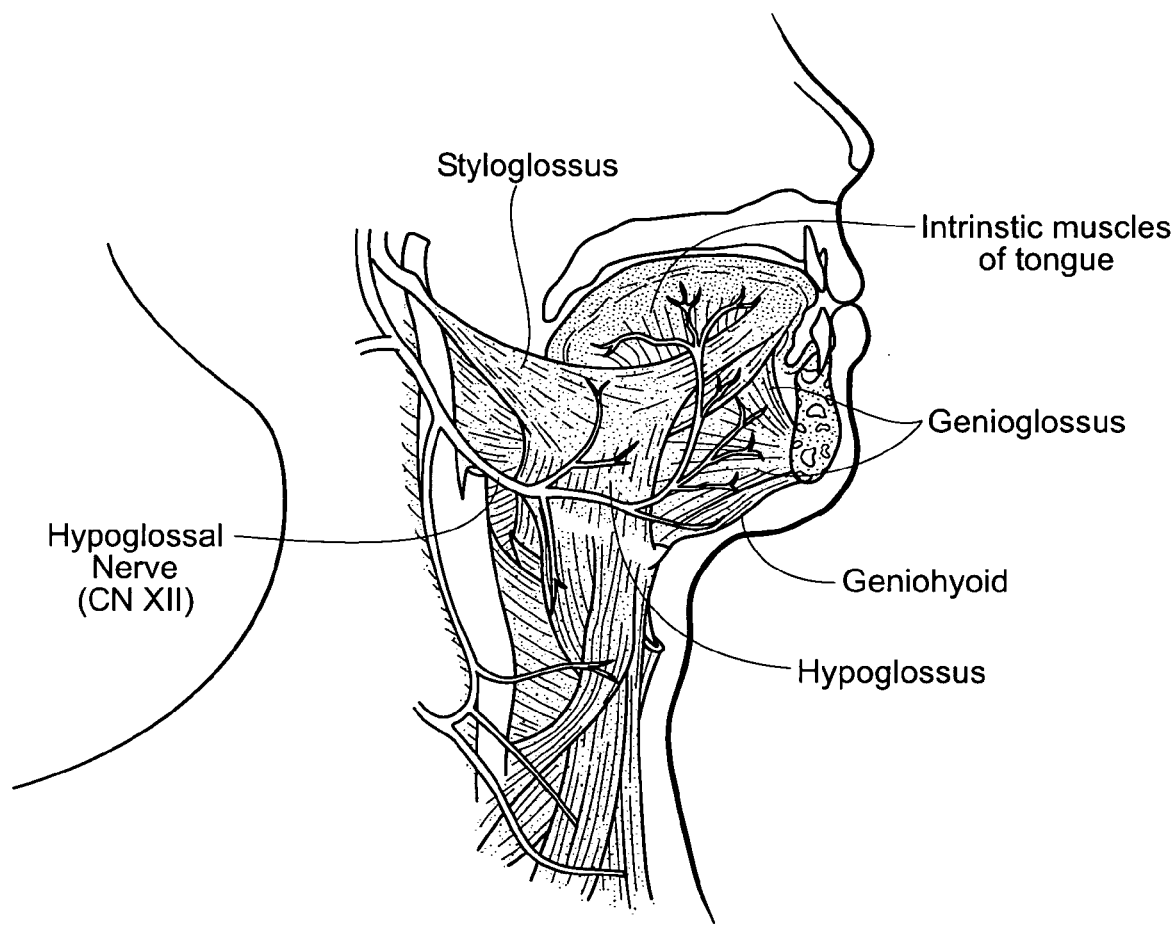
FIG. 41 is an anatomic view of the head and neck region of a human and showing the intrinsic and extrinsic muscles of the tongue, and the hypoglossal nerve that innervates these muscles.

The hypoglossal nerve is the main nerve that innervates the intrinsic and extrinsic muscles of the tongue. As FIG. 41 shows, the hypoglossal nerve leaves the skull through the hypoglossal canal and passes inferolaterally to the angle of the mandible. From here it curves anteriorly where it separates into many branches that supply the intrinsic muscles and three of the four extrinsic muscles of the tongue (the hyoglossus, genioglossus, and geniohyoid).

It has been discovered that stimulation of the hypoglossal nerve and/or its branches with one or more electrodes can be used to affect the muscles of the upper airway. Electrical stimulation of the hypoglossal nerve is known to affect the genioglossus and the geniohyoid muscles. These muscles are the primary muscles involved in dilating the upper airway. When the genioglossus contracts, the tongue protrudes outward, causing the airway to dilate.

Figure 42:
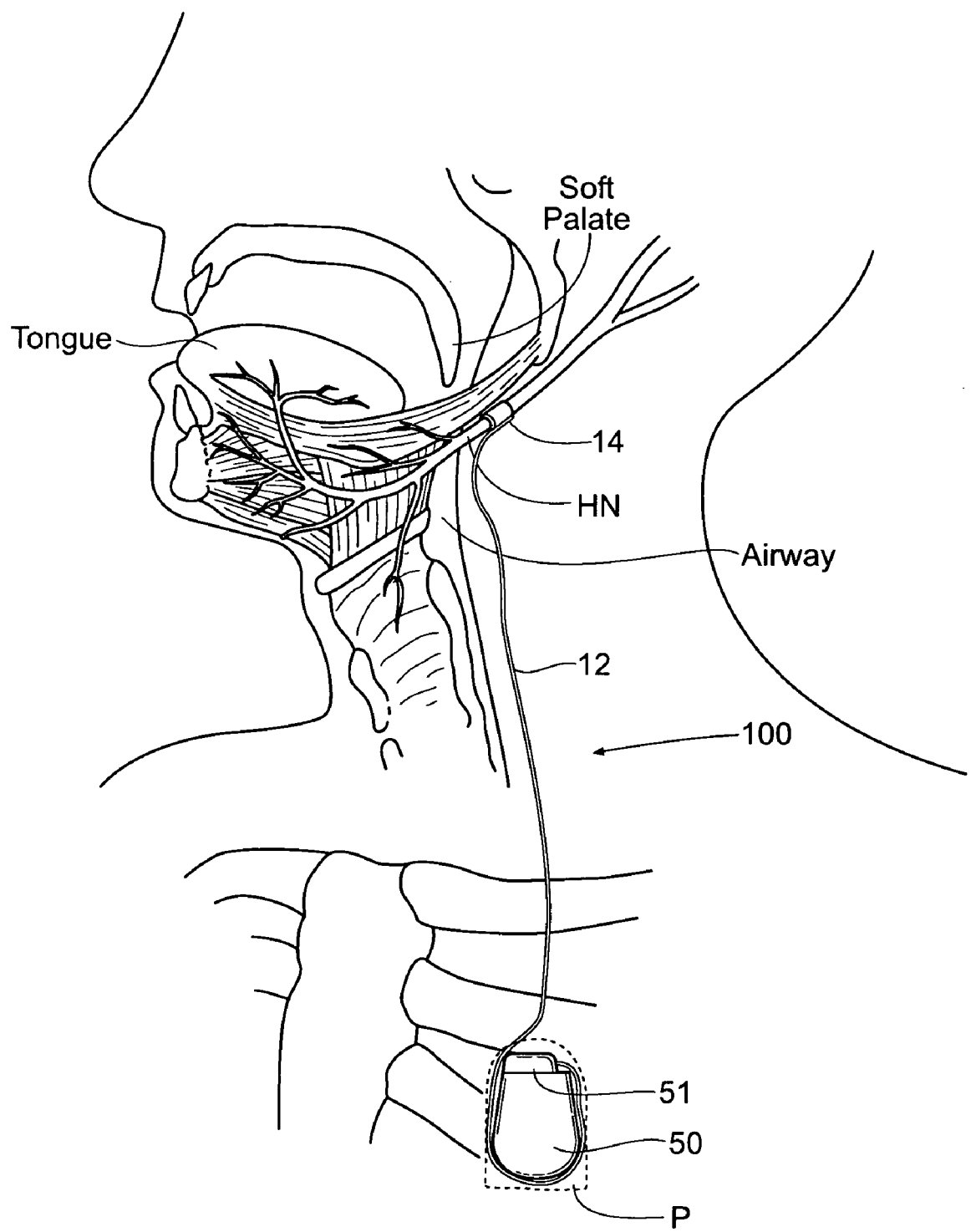
FIG. 42 is an anatomic view of the head and neck region of a human and showing an implanted stimulation assembly that may be used for the treatment of sleep apnea, the assembly including an implantable pulse generator, a molded nerve cuff positioned about the hypoglossal nerve, and a lead electrically coupling the electrodes within the nerve cuff to the pulse generator.

FIG. 42 shows a system 100 for stimulating nerves and/or muscles, such as the hypoglossal nerve, for functional treatment, such as for the treatment of OSA. The assembly includes the implantable split nerve cuff system 10 coupled to an implantable pulse generator or IPG 50. The distal end of the lead 12 carries the split cuff 14 (see FIG. 1). It is to be appreciated that the system 100 may be used with cuffs 16 and 70 as well, and variations thereof. The lead 12, cuff 14, and implantable pulse generator 50 are shown implanted within a tissue region T of a human or animal body.

FIG. 42 shows the lead 12, cuff 14, and the implantable pulse generator 18 implanted within the neck and thorax region of a human body. In this exemplary embodiment, the electrode cuff 14 is implanted in electrical conductive contact with the hypoglossal nerve HN, to apply electrical stimulation to the hypoglossal nerve HN. The implantable pulse generator 50 includes a connection header 51 that desirably carries a plug-in receptacle 48 for the connector 28 on the proximal end of the lead 12. In this way, the lead 12 electrically connects the cuff 14 to the implantable pulse generator 50.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. An implantable cuff electrode comprising:
   an inner elastic body having a cylindrical inside surface and an exterior surface extending longitudinally along a length, the inner elastic body having a plurality of apertures formed radially therethrough at circumferentially spaced locations, wherein the inner elastic body includes a first longitudinal split extending through the length,
   a plurality of electrodes, each electrode being positioned at least partially within a corresponding aperture,
   an insulating material including a second longitudinal split, the insulating material being positioned over all of the exterior surface of the inner elastic body and the plurality of electrodes, wherein the second longitudinal split is aligned with the first longitudinal split, and wherein the first longitudinal split and the second longitudinal split together form an expandable access point to enable positioning of the cuff electrode over a target nerve, and
   a cover tube positioned over the insulating material.

2. The implantable cuff electrode of claim 1 wherein the insulating material is secured to at least a portion of the inner elastic body.

3. The implantable cuff electrode of claim 1 wherein the cover tube is secured to at least a portion of the insulating material.

4. The implantable cuff electrode of claim 1 wherein the cover tube includes a third longitudinal split extending the length of the cover tube.

5. The implantable cuff electrode of claim 4 wherein the first longitudinal split and the third longitudinal split are circumferentially out of phase.

6. The implantable cuff electrode of claim 1 wherein the cover tube extends in a range of about 350 degrees to about 540 degrees from end to end.

7. The implantable cuff electrode of claim 1 wherein the inside surface of the inner elastic body is configured for placement around the target nerve.

8. The implantable cuff electrode of claim 1 wherein at least one of the plurality of electrodes includes an electrically conductive surface that extends beyond or is radially recessed from the inside surface of the inner elastic body.

9. A system for neuronal recording and/or stimulating and/or blocking, the system comprising:
   an implantable lead having a proximal end and a distal end,
   a cuff electrode coupled to the distal end of the lead, the cuff electrode comprising
   an inner elastic body having a cylindrical inside surface and an exterior surface extending longitudinally along a length, the inner elastic body having a plurality of apertures formed radially therethrough at circumferentially spaced locations, wherein the inner elastic body includes a first longitudinal split extending through the length,
   a plurality of electrodes, each electrode being positioned at least partially within a corresponding aperture,
   an insulating material including a second longitudinal split, the insulating material being positioned over all of the exterior surface of the inner elastic body and the plurality of electrodes, wherein the second longitudinal split is aligned with the first longitudinal split, and wherein the first longitudinal split and the second longitudinal split together form an expandable access point to enable positioning of the cuff electrode over a target nerve, and
   a cover tube positioned over the insulating material,
   the lead encapsulating at least one wire element extending to the proximal end of the lead, wherein the at least one wire element is electrically coupled to at least one of the plurality of electrodes, and
   the proximal end of the lead being coupled to a stimulation pulse generator.

10. The system according to claim 9:
    wherein the proximal end of the lead comprises an implantable IS-1 connector.

11. The system according to claim 9:
    further including means to anchor the distal portion of the lead to surrounding tissue.

* * * * *